US010352928B2

(12) United States Patent
Vallée-Bélisle et al.

(10) Patent No.: US 10,352,928 B2
(45) Date of Patent: Jul. 16, 2019

(54) STERIC-HINDRANCE HYBRIDIZATION SYSTEMS, ASSAYS AND METHODS ASSOCIATED THERETO

(71) Applicant: VALORISATION-RECHERCHE, LIMITED PARTNERSHIP, Montréal (CA)

(72) Inventors: Alexis Vallée-Bélisle, Outremont (CA); Sahar Sadat Mahshid, Barrie (CA)

(*) Notice: Subject to any disclaimer, the term of this patent is extended or adjusted under 35 U.S.C. 154(b) by 9 days.

(21) Appl. No.: 15/301,075

(22) PCT Filed: Apr. 2, 2015

(86) PCT No.: PCT/CA2015/050269
§ 371 (c)(1),
(2) Date: Sep. 30, 2016

(87) PCT Pub. No.: WO2015/149184
PCT Pub. Date: Oct. 8, 2015

(65) Prior Publication Data
US 2017/0045503 A1 Feb. 16, 2017

Related U.S. Application Data

(60) Provisional application No. 61/975,231, filed on Apr. 4, 2014.

(51) Int. Cl.
| G01N 33/53 | (2006.01) |
| C12Q 1/68 | (2018.01) |
| G01N 33/542 | (2006.01) |
| C12Q 1/6827 | (2018.01) |
| G01N 27/327 | (2006.01) |

(52) U.S. Cl.
CPC ......... G01N 33/542 (2013.01); C12Q 1/6827 (2013.01); G01N 27/3277 (2013.01); G01N 2458/10 (2013.01)

(58) Field of Classification Search
CPC .......... C12Q 1/68; C07H 21/00; G01N 33/53
See application file for complete search history.

(56) References Cited

U.S. PATENT DOCUMENTS

| 3,935,074 A * | 1/1976 | Rubenstein .......... G01N 33/542 435/188 |
| 2007/0154909 A1 | 7/2007 | Xiao et al. |
| 2008/0199863 A1* | 8/2008 | Haake .................... C12Q 1/689 435/6.11 |
| 2013/0288923 A1* | 10/2013 | Vallee-Belisle ...... C12Q 1/6818 506/9 |
| 2015/0247816 A1* | 9/2015 | Bhansali ............ G01N 27/3275 205/782 |

FOREIGN PATENT DOCUMENTS

| CA | 2818556 | 5/2012 |
| WO | 2007/120299 | 10/2007 |
| WO | 2012/071344 | 5/2012 |
| WO | 2012071344 A2 | 5/2012 |

OTHER PUBLICATIONS

Maehashi et al;.., Label-Free Protein Biosensor Based on Aptamer-Modified Carbon Nanotube Field-Effect Transistors. Analytical Chemistry 79:782 (Year: 2007).*
Wang, J., Electrochemical biosensors: Towards point-of-care cancer diagnostics. Bisensors & Bioelectronics 21 :1887 (Year: 2006).*
Xu et al.,Electrostatic repulsion and steric hindrance effects of surface probe density on deoxyribonucleic acid (DNA)/peptide nucleic acid (PNA) hybridization. Thin Solid Films 516: 8634 (Year: 2008).*
Zhang et al., Electrochemical Aptasensor Based on Proximity-Dependent Surface Hybridization Assay for Single-Step, Reusable, Sensitive Protein Detection. JACS 129: 15,448 (Year: 2007).*
Brunel, F. M.; Zwick, M. B.; Cardoso, R. M. F.; Nelson, J. D.; Wilson, I. A.; Burton, D. R.; Dawson, P. E. J. Virol. 2006, 80, 1680-1687.
Cash, K. J.; Ricci, F.; Plaxco, K. W. Chem. Comm. 2009a, 41, 6222-4.
Cash, K. J.; Ricci, F.; Plaxco, K. W. J Am Chem Soc 2009b, 131, 6955-7.
Fan C, Plaxco KW, Heeger AJ. Electrochemical interrogation of conformational changes as a reagentless method for the sequence-specific detection of DNA. Proc Natl Acad Sci U S A. Aug. 5, 2003;100(16):9134-7. Epub Jul. 16, 2003.
Idili, A.; Amodio, A.; Vidonis, M.; Feinberg-Somerson, J.; Castronovo, M.; Ricci, F. Analytical chemistry 2014, 86, 9013.
Lass-Napiorkowska A, Heyduk E, Tian L, Heyduk T. Detection methodology based on target molecule-induced sequence-specific binding to a single-oligonucleotideed oligonucleotide. Anal Chem. Apr. 3, 2012;84(7):3382-9. doi: 10.1021/ac3001034. Epub Mar. 22, 2012.
O'Connor, S. D.; Olsen, G. T.; Creager, S. E. Journal of Electroanalytical Chemistry 1999, 466, 197.
Ricci F, Adornetto G, Palleschi G, A review of experimental aspects of electrochemical immunosensors, Electrochimical Acta, vol. 84, Dec. 1, 2012, pp. 74-83.
Vallée-Bélisle, A.; Ricci, F.; Uzawa, T.; Xia, F.; Plaxco, K. W. J Am Chem Soc 2012, 134, 15197-200.

(Continued)

Primary Examiner — Ethan C Whisenant
(74) Attorney, Agent, or Firm — Marie-Helene Rochon

(57) ABSTRACT

The present disclosure provides target detection and quantification systems as well as related methods based on the use of steric hindrance (either created by the target itself or a macromolecular entity used to bind to the target) to prevent or limit the hybridizing between an anchoring oligonucleotide (associated to a substrate) and a signaling oligonucleotide or a combination of signaling oligonucleotides (capable of specifically binding the target or the macromolecular entity).

20 Claims, 14 Drawing Sheets
Specification includes a Sequence Listing.

(56) References Cited

OTHER PUBLICATIONS

White, R. J.; Phares, N.; Lubin, A. A.; Xiao, Y.; Plaxco, K. W. Langmuir 2008, 24, 10513-8.

Xiao, Y.; Lai, R. Y.; Plaxco, K. W. Preparation of Electrode-Immobilized, Redox-Modified Oligonucleotides for Electrochemical DNA and Aptamer-Based Sensing. Nat Protoc 2007, 2, 2875-2880.

Zhang H, Li F, Dever B, Li XF, Le XC, DNA-mediated homogeneous binding assays for nucleic acids and proteins, Chem Rev. Apr. 10, 2013;113(4):2812-41. doi: 10.1021/cr300340p. Epub Dec. 11, 2012.

Yoshizumi, J. et al., << Target-induced stand release (TISR) from aptamer-DNA duplex: A general strategy for electronic detection of biomolecules ranging from a small molecule to a large protein >> The Analyst, Mar. 2008 (Mar. 2008), vol. 133, No. 3, pp. 323-325, ISSN:0003-2654.

Sassolas, A. et al., << Electrochemical aptasensors >> Electroanalysis, Jun. 2009 (Jun. 2009), vol. 21, No. 11, pp. 1237-1250, ISSN:1521-4109.

White RJ et al., Wash-free, electrochemical platform for the quantitative, multiplexed detection of specific antibodies. Anal Chem. Jan. 17, 2012;84(2)1098-103.

Lubin AA et al., Folding-based electrochemical biosensors: the case for responsive nucleic acid architectures. Acc Chem Res. Apr. 20, 2010;43(4):496-505.

Mahshid SS et al., A Highly Selective Electrochemical DNA-Based Sensor That Employs Steric Hindrance Effects to Detect Proteins Directly in Whole Blood. J Am Chem Soc. Dec. 23, 2015;137(50):15596-9.

Mahshid, Camiré, Ricci, Vallée-Bélisle. A Highly Selective Electrochemical DNA-Based Sensor That Employs Steric Hindrance Effects to Detect Proteins Directly in Whole Blood. J Am Chem Soc. Dec. 23, 2015;137(50):15596-9. doi: 10.1021/jacs.5b04942. Epub Sep. 24, 2015.

Mahshid, Camiré, Ricci, Vallée-Bélisle. Supporting information for: A Highly Selective Electrochemical DNA-Based Sensor That Employs Steric Hindrance Effects to Detect Proteins Directly in Whole Blood.

Li H, Arroyo-Currás N, Kang D, Ricci F, Plaxco KW. Dual-Reporter Drift Correction to Enhance the Performance of Electrochemical Aptamer-Based Sensors in Whole Blood. J Am Chem Soc. Dec. 14, 2016;138(49):15809-15812. Epub Nov. 22, 2016.

White RJ, Kallewaard HM, Hsieh W, Patterson AS, Kasehagen JB, Cash KJ, Uzawa T, Soh HT, Plaxco KW. Wash-free, electrochemical platform for the quantitative, multiplexed detection of specific antibodies. Anal Chem. Jan. 17, 2012;84(2):1098-103. doi: 10.1021/ac202757c. Epub Jan. 3, 2012.

Lubin AA, Plaxco KW. Folding-based electrochemical biosensors: the case for responsive nucleic acid architectures. Acc Chem Res. Apr. 20, 2010;43(4):496-505. doi: 10.1021/ar900165x.

* cited by examiner

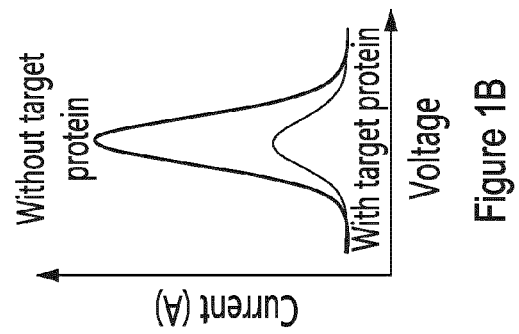
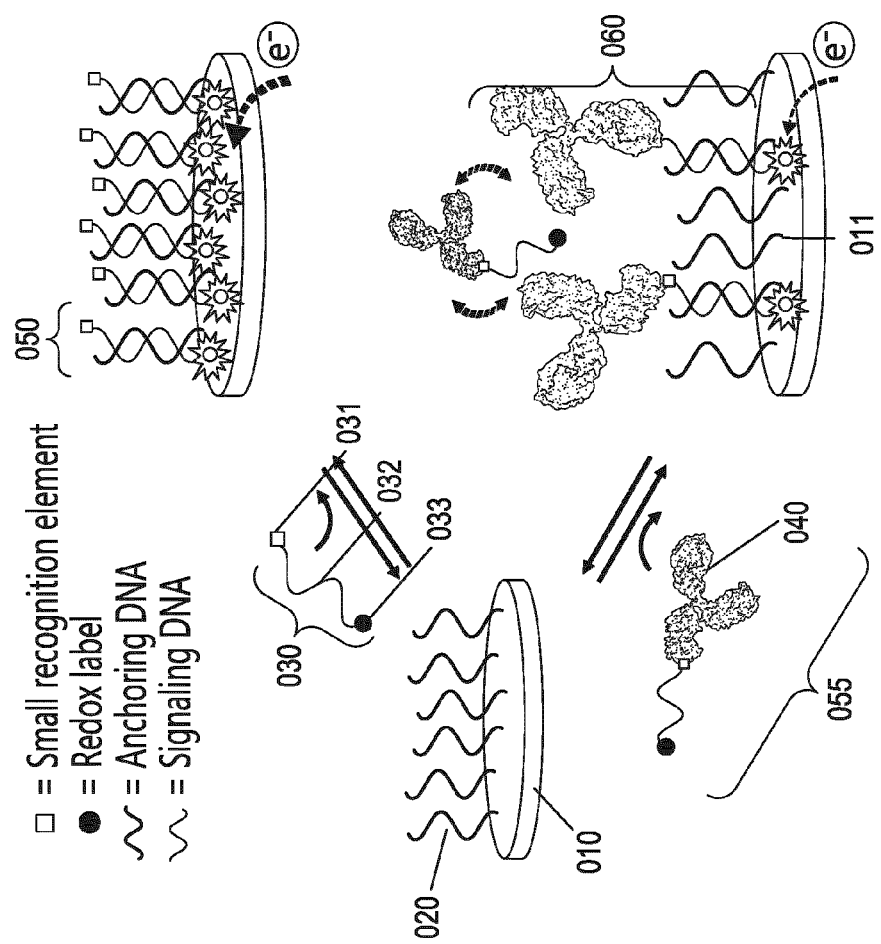
Figure 1A
Figure 1B

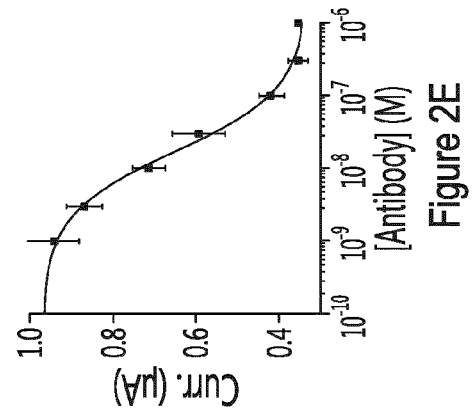
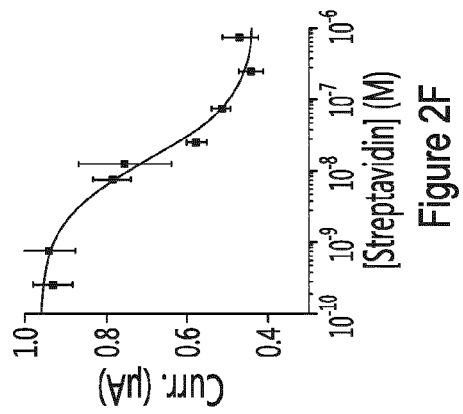
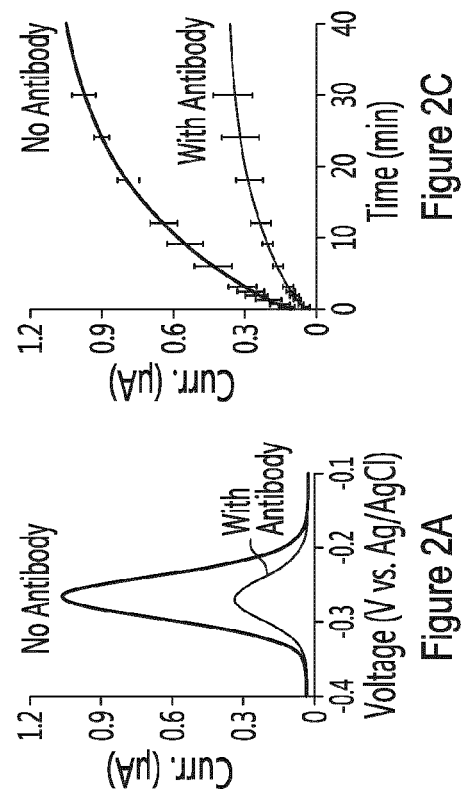
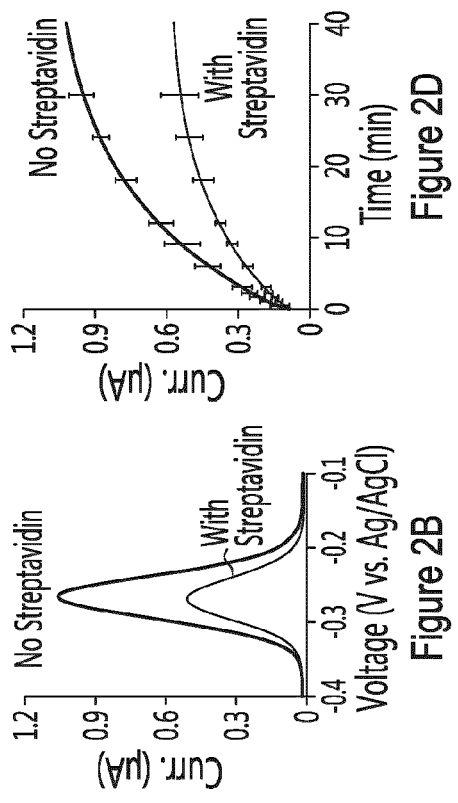

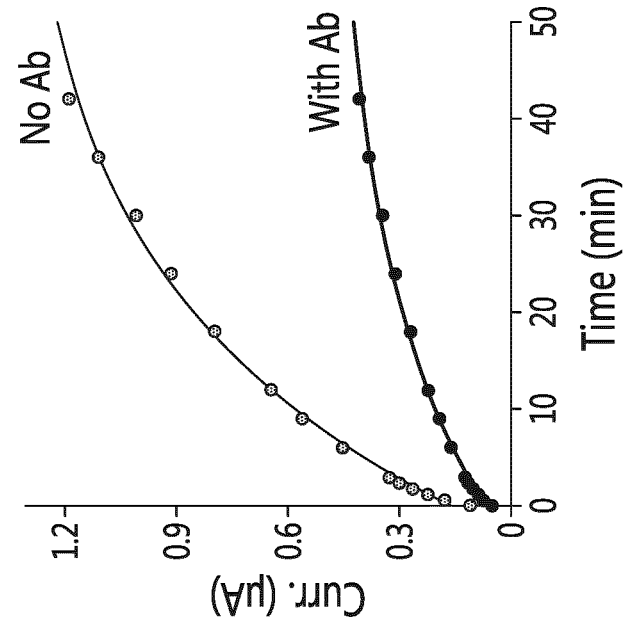
Figure 9A2
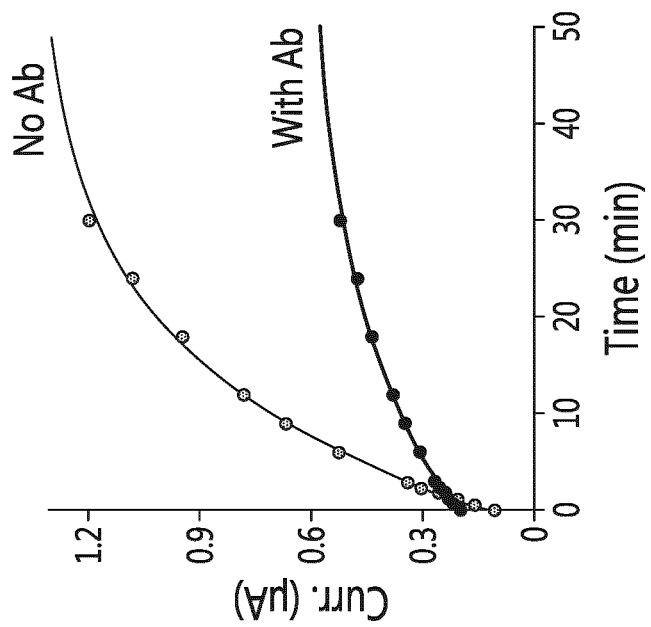
Figure 9A1

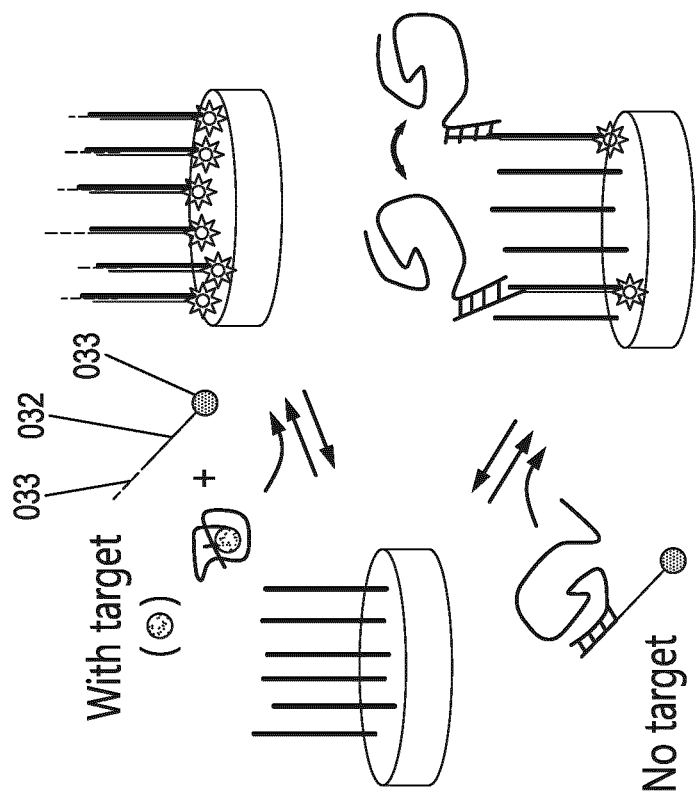
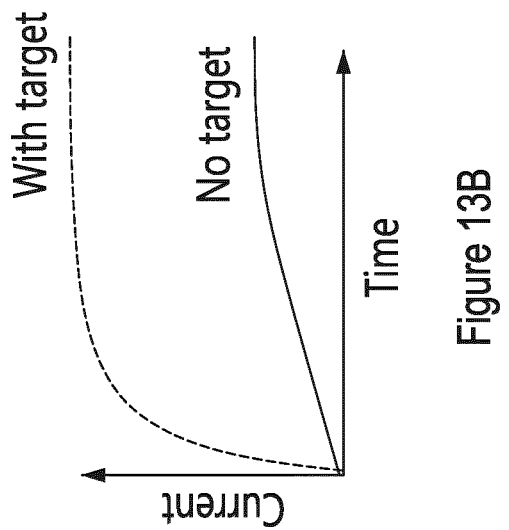
Figure 13A
Figure 13B

SEQUENCE LISTING

```
<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: Anchoring oligonucleotide Dig/biotin

<400> SEQUENCE: 1
aaggaaaggg aagaag                                                   16

<210> SEQ ID NO 2
<211> LENGTH: 16
<212> TYPE: DNA
<213> ORGANISM: Artificial Sequence
<220> FEATURE:
<223> OTHER INFORMATION: Anchoring oligonucleotide Ctrl

<400> SEQUENCE: 2
gagagggaaa aaggag                                                   16

<210> SEQ ID NO 3
<211> LENGTH: 16
<212> TYPE: DNA
<213> ORGANISM: Artificial Sequence
<220> FEATURE:
<223> OTHER INFORMATION: Anchoring oligonucleotide DNP

<400> SEQUENCE: 3
tcagtaggag agtgga                                                   16

<210> SEQ ID NO 4
<211> LENGTH: 16
```

```
<212> TYPE: DNA
<213> ORGANISM: Artificial Sequence
<220> FEATURE:
<223> OTHER INFORMATION: Signaling oligonucleotide Dig/biotin

<400> SEQUENCE: 4
cttcttccct ttcctt                                                   16

<210> SEQ ID NO 5
<211> LENGTH: 16
<212> TYPE: DNA
<213> ORGANISM: Artificial Sequence
<220> FEATURE:
<223> OTHER INFORMATION: Signaling oligonucleotide DNP

<400> SEQUENCE: 5
tccactctcc tactga                                                   16

<210> SEQ ID NO 6
<211> LENGTH: 16
<212> TYPE: DNA
<213> ORGANISM: Artificial Sequence
<220> FEATURE:
<223> OTHER INFORMATION: Signaling oligonucleotide Ctrl

<400> SEQUENCE: 6 ctccttttc cctctc                                                    16

<210> SEQ ID NO 7
<211> LENGTH: 16
<212> TYPE: DNA
<213> ORGANISM: Artificial Sequence
<220> FEATURE:
<223> OTHER INFORMATION: Anchoring oligonculeotide 10A1, 10A3 and 10A4

<400> SEQUENCE: 7
tcagtaggag agtgga                                                   16

<210> SEQ ID NO 8
<211> LENGTH: 16
<212> TYPE: DNA
<213> ORGANISM: Artificial Sequence
<220> FEATURE:
<223> OTHER INFORMATION: Anchoring oligonucleotide 10A2

<400> SEQUENCE: 8
ccggaaaggg aagaag                                                   16

<210> SEQ ID NO 9
<211> LENGTH: 16
<212> TYPE: DNA
<213> ORGANISM: Artificial Sequence
<220> FEATURE:
<223> OTHER INFORMATION: Signaling oligonucleotide 10A1

<400> SEQUENCE: 9
tccactctcc tactga                                                   16

<210> SEQ ID NO 10
<211> LENGTH: 18
<212> TYPE: PRT
<213> ORGANISM: Artificial Sequence
<220> FEATURE:
<223> OTHER INFORMATION: Signaling oligonucleotide moiety for binding
      AE10 antbodies

<400> SEQUENCE: 10
```

```
Asn Trp Phe Asp Ile Thr Asn Trp Leu Trp Tyr Ile Lys Lys Lys
1               5                   10                  15

Gly Ser

<210> SEQ ID NO 11
<211> LENGTH: 16
<212> TYPE: DNA
<213> ORGANISM: Artificial Sequence
<220> FEATURE:
<223> OTHER INFORMATION: Signaling oligonucleotide 10A3, 10A4

<400> SEQUENCE: 11
ccttaacccg tttgcc                                                    16

<210> SEQ ID NO 12
<211> LENGTH: 32
<212> TYPE: DNA
<213> ORGANISM: Artificial Sequence
<220> FEATURE:
<223> OTHER INFORMATION: Signaling oligonucleotide 10A3, 10A4

<400> SEQUENCE: 12
ggcaaacggg ttaaggtcca ctctcctact ga                                  32
```

STERIC-HINDRANCE HYBRIDIZATION SYSTEMS, ASSAYS AND METHODS ASSOCIATED THERETO

CROSS-REFERENCE TO RELATED APPLICATIONS AND DOCUMENTS

This application claims priority from U.S. provisional application 61/975,231 filed on Apr. 4, 2014, the content of which is incorporated herein in its entirety. This application also comprises a sequence listing filed electronically, the content of which is incorporated herein in its entirety.

TECHNOLOGICAL FIELD

This present disclosure relates to the detection and optional quantification of targets based on the use of steric hindrance created upon the formation of a complex between an anchoring oligonucleotide, a signaling oligonucleotide and a macromolecular entity (which can either be the target itself or capable of binding to the target).

BACKGROUND

The development of rapid, low cost, point-of-care (POC) approaches for the quantitative detection of multiple proteins or biomarkers such as antibodies would drastically impact global health by allowing more frequent testing and by improving the penetration of molecular diagnostics into the developing world. Up to date, current methods for the quantitative detection of proteins, such as antibodies, still mostly rely on ELISAs, Western Blots and polarization assays, which are multi-step, wash- and reagent-intensive processes that necessitate specialized technicians and require several hours before completion. Alternative point-of-care approaches, such as immunochemical dipsticks, display important advantages in terms of ease-of-use and affordability. Unfortunately, however, these remain hardly multiplexable and their results are mostly qualitative thus open to subjective interpretation.

Over the last decade, two main categories of biosensing devices have been explored in order to achieve multiplexed, quantitative, point-of-care (POC) protein detection: lab-on-chip devices and single-step homogeneous assays. Lab-on-a-chip devices (e.g. microfluidic devices), which integrate and automate multiple steps onto a unique device, have shown great promise for POC multiplex detection in recent years. However, their high cost, requirement for reagents and relatively complex handling still provides important hurdles for their transition into the real world. Single-step homogeneous assays, on the other hand, which necessitate simple mix and read procedure without the necessity to process samples by separation or washing steps, represent another promising avenue for point-of-care biosensing. Unfortunately, however, few homogeneous assays are selective enough to enable the single-step detection of protein markers directly in unprocessed whole blood.

Numerous single-step homogeneous assays for protein detection have been developed in recent years. Those methods include protein-based assays, and DNA-based assays. Among these different approaches, DNA-based electrochemical sensors (E-DNA) have shown great promise for the transition into the real world. These sensors are typically rapid, reagent-less, multiplexable and versatile, allowing detection of nucleic acids, proteins and small analytes. They take advantage of the high specificity and programmability of DNA in addition to permitting easy electrochemical measurements directly in complex samples such as blood serum using relatively inexpensive potentiostats. Unfortunately, however, these sensors still display limitations that preclude their transition into real life applications. These include rapid signal drifts in the first minutes when the sensor is immersed in whole blood and low nano-amp electrochemical signal output.

A versatile DNA-based electrochemical switch was further developed that supports the rapid, quantitative detection of large macromolecules such as antibodies directly in whole blood at clinically relevant, low-nanomolar concentrations (Vallée-Bélisle et al., 2012). Unfortunately, however, this DNA switch only performs well at low surface density on the sensor head, a condition required in order to ensure that each single switch is activated by a large macromolecule that often span up to dozens of nm (e.g., antibodies: 12 nm). These low density sensors therefore only generate low $nA/cm^2$ current densities, which can only be detected by expensive, laboratory-grade potentiostats. Furthermore, these switch-based DNA sensors remain relatively hard to synthetize since they require the addition of many chemical moieties (e.g. electro-active elements, C6-thiol, frame-inversion, epitopes . . . ) and typically require long equilibration time (minutes) in their working media (for example, whole blood) before they are stable enough to enable precise measurements.

Various technologies for detecting various targets were developed but their applications are limited. International application WO 2012/071344 by Vallée-Bélisle et al. describes the use of a unimolecular probe for detecting and quantifying macromolecules and other analytes. The technology described therein is based on conformational modification of the unimolecular probe upon binding to the target for triggering a detectable signal. However, this technology is limited to the detection of targets or a combination of targets capable of binding simultaneously to two distinct target-binding moieties on the unimolecular probe to induce a conformational modification. The publication of Lass-Napiorkowska et al. (2012) describes a combination of three oligonucleotides which produce a FRET signal upon binding to the target. However, much like the PCT application to Vallée-Bélisles described above, this technology is limited to the detection of targets or a combination of targets capable of binding simultaneously two target-binding moieties present on distinct oligonucleotides to induce the FRET signal. International application WO 2007/120299 by Xiao et al. describes the use of a signal-on architecture for detecting targets. However, this technology is limited to the detection of targets which can specifically bind a nucleic acid molecule. The publication of Fan et al. (2003) describes the use of a single stem-containing oligonucleotide which changes its conformation upon binding to the target. Much like the PCT application to Xiao et al. described above, this technology is limited to the detection of targets which can bind to nucleic acid molecules.

It would be highly desirable to be provided with an assay for the detection/quantification of various targets (which may not necessarily be able to bind to two distinct target-binding moieties or to nucleic acid molecules). It would also be desirable with an assay for the detection/quantification of targets in complex mixtures, such as whole blood and food.

BRIEF SUMMARY

The present disclosure concerns the use of steric hindrance to prevent or limit the association between two adjacent oligonucleotide complexes to detect, and in some embodiments quantify, the presence of a target in a sample. As it will be shown below, a combination at least three distinct components are used: a substrate comprising anchoring oligonucleotides and a unimolecular or modular signaling oligonucleotides being substantially complementary to the anchoring oligonucleotides. In some embodiment, the system can also comprise a macromolecular entity for binding the target. The signaling oligonucleotides also comprise a moiety for binding the macromolecular entity (either to bind the target directly or to bind the target indirectly through a macromolecular entity capable of directly binding the target) and a reporter moiety (capable of modulating a signal in conjunction with the surface of the substrate when the anchoring oligonucleotide and the signaling oligonucleotide are hybridized). The anchoring oligonucleotide is associated to the surface of the substrate at a density which prevents or limits the formation of a complex between at least one anchoring oligonucleotide, at least one signaling oligonucleotide and the macromolecular entity at two adjacent locations on the substrate. In some embodiments, the assay and methods described herewith can be used in a multiplex format and/or in complex biological mixtures, such as whole blood or food.

According to a first aspect, the present disclosure provides a system for detecting a target in sample. The system comprises (i) a plurality of anchoring oligonucleotides each having a nucleic acid sequence, a first end and a second free end; (ii) a first substrate having a surface associated with, at a plurality of discrete locations, each of the first end of the plurality of anchoring oligonucleotides; and (iii) a plurality of signaling oligonucleotides. Each of the signaling oligonucleotide (i) has a core nucleic acid sequence which is substantially complementary to a region of each of the anchoring oligonucleotides and is capable of hybridizing with the anchoring oligonucleotide; (ii) has a first end being associated with a moiety for binding a macromolecular entity; (iii) has a second end being associated with a reporter moiety; and (iv) is configured such that, upon hybridizing with the anchoring oligonucleotide, the second end of the signaling oligonucleotide is located in the vicinity of the first end of the anchoring oligonucleotide. In the systems described herein, the density of the plurality of anchoring oligonucleotides on the first substrate prevents or limits the formation of a complex between at least one anchoring oligonucleotide, at least one signaling oligonucleotide and the macromolecular entity at two adjacent locations on the first substrate. In an embodiment, the target is the macromolecular entity, such as a polypeptide (an antibody for example). In such embodiment, the moiety for binding the macromolecular entity can comprise an epitope specifically recognized by the antibody. In another embodiment, the system further comprises a macromolecular entity capable of specifically binding the target (an antibody or an aptamer for example). In such embodiment, the moiety for binding the macromolecular entity can be the target or comprise a nucleic acid molecule for hybridizing with the macromolecular entity (the aptamer for example). In yet another embodiment, the first end (such as a nucleic acid terminus) of each of the anchoring oligonucleotides is covalently associated to the surface of the first substrate. In still another embodiment, each of the anchoring oligonucleotide comprises at least 10 nucleic acid bases. In a further embodiment, the first substrate is a metallic electrode (a gold electrode for example). In another embodiment, the core nucleic acid sequence of the signaling oligonucleotide is complementary to the nucleic acid sequence of the anchoring oligonucleotide over the entire length of the anchoring oligonucleotide. In still a further embodiment, each of the signaling oligonucleotide comprises at least 10 nucleic acid bases. In an embodiment, the reporter moiety is a redox-reporter (methylene blue for example).

According to a second aspect, the present disclosure provides a system for detecting more than one target, e.g. in a multiplex format. The multiplex system comprises the system described herein and further comprises (i) a plurality of types of anchoring oligonucleotides each type of anchoring oligonucleotide having a distinct nucleic acid sequence, a first end and a second free end; (ii) a plurality of substrates, each of the substrate having a surface associated with, at a plurality of discrete locations, with the first end of a single type of anchoring oligonucleotides and each of the substrates having a different type of anchoring oligonucleotide; and (iii) a plurality of types of signaling oligonucleotides. In the multiplex system, each type of the signaling oligonucleotides (i) has a core nucleic acid sequence substantially complementary to a region of a corresponding anchoring oligonucleotides and is capable of hybridizing with the corresponding anchoring oligonucleotide; (ii) has a first end being associated with a distinct moiety for binding a distinct macromolecular entity; (iii) has a second end being associated with a reporter moiety; and (iv) is configured such that, upon hybridizing with the corresponding anchoring oligonucleotide, the second end of the signaling oligonucleotide is located in the vicinity of the first end of the anchoring oligonucleotide. In the multiplex system, the density of the anchoring oligonucleotides on each of the plurality substrates prevents or limits the formation of a complex between at least one anchoring oligonucleotide, at least one signaling oligonucleotide and the macromolecular entity at two adjacent locations on each of the plurality of substrates.

In a third aspect, the present disclosure provides an optional control or reference system. The control/reference system comprises the system described herein (monoplex or multiplex format) and also comprises (i) a second substrate having a surface associated, at a plurality of discrete locations, with each of the first end of the plurality of anchoring oligonucleotides; and (ii) a plurality of negative control oligonucleotides. In the control/reference system, each of the plurality of the negative control oligonucleotides (i) has a core nucleic acid sequence substantially complementary to a region of the anchoring oligonucleotide and is capable of hybridizing with the anchoring oligonucleotide; (ii) has a first end lacking the moiety for binding a macromolecular entity; (iii) has a second end having the reporter moiety; and (iv) is configured such that, upon hybridizing with the anchoring oligonucleotide the second end of the signaling oligonucleotide is located in the vicinity of the first end of the anchoring oligonucleotide. In the control/reference system, the density of the plurality of the anchoring oligonucleotides on the second substrate is similar to the density of the plurality of the anchoring oligonucleotides on the first substrate.

In a fourth aspect, the present disclosure provides a method for the detection of a target (or a plurality of targets) in a sample. Broadly, the method comprises (i) providing the sample suspected of having the target (or the plurality of targets); (ii) providing the system of described herein; (iii) providing or determining a control amount of the plurality of anchoring oligonucleotides having hybridized with the plurality signaling oligonucleotides in the system in the absence of the target; (iv) contacting the sample with the system; (v) determining a test amount of the plurality of anchoring oligonucleotides having hybridized with the plurality signaling oligonucleotides in the system in the presence of the sample; (vi) characterizing the sample has having the target if it is determined that the test amount is lower than the control amount and as lacking the target if it is determined that the test amount is equal to or higher than the control amount. In an embodiment, the method further comprises quantifying the concentration of the target in the sample based on the comparison of the first amount and the second amount. In another embodiment, the method comprises determining the control amount by (i) contacting a control sample known to lack the target with the system described herein and determining the amount of the plurality of anchoring oligonucleotides having hybridized with the plurality of signaling oligonucleotides; or contacting the sample with the control/reference system described herein and determining the amount of the plurality of the anchoring oligonucleotides having hybridized with the plurality signaling oligonucleotides on the second substrate. In an embodiment, the method further comprises determining the test amount and/or the control amount electrochemically. In still another embodiment, the sample is a biological sample (such as whole blood). In yet another embodiment, the sample is a food sample. In still another embodiment, the target is a bacteria or a virus.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 provides a schematic representation of an electrochemical Steric-Hindrance Hybridization Assay (eSHHA). (A) The eSHHA is composed of a densely-packed surface-bound anchoring DNA oligonucleotide (bold line) and a free complementary signaling DNA oligonucleotide (regular line). The signaling oligonucleotide is labeled at the two ends with a small recognition element (□, also referred to as a moiety for binding a macromolecular entity) and a signaling, active moiety (● or ○, also referred to as a reporter moiety). In absence of macromolecular target macromolecule (top), the signaling oligonucleotides are free to interact with all the anchoring oligonucleotides thus generating a large electrochemical current (bold curve in B) by bringing multiple redox label near the electrode's surface. In the presence of macromolecular targets (bottom), the signaling oligonucleotides will be captured by the target through binding to the recognition element, thus significantly limiting their ability to hybridize on the electrode surface due to steric hindrance effect (regular curve in B). (B) Representation of the current (measured in A) in function of voltage for the eSSHA (described in A) in the presence (regular line) and in the absence (bold line) of the macromolecular target.

FIG. 2 illustrates that an antibody and streptavidin can be used as macromolecular entities (targets) in eSHHA. Dig-(top) or biotin-(bottom) labeled signaling oligonucleotides were used to detect their respective target (anti-Dig antibodies and streptavidin respectively). (A-B) In absence of the target, the signaling oligonucleotides are free to hybridize to the complementary anchoring oligonucleotides, thus generating high electrochemical current by bringing numerous redox-active MB next to the gold surface (bold curves). In presence of 100 nM anti-Dig antibody (regular curves in A and B) or streptavidin, fewer signaling oligonucleotides reach the gold surface due to steric hindrance, thus generating a lowered current. (C-D) Measurements of current (μA) in function of time (min) are shown for the different systems in the presence and absence of the macromolecular targets. The hybridization rate of the signaling oligonucleotide is not affected by the presence of the macromolecular target ($t_{1/2}$ Antibody=11.6 and 10.5 min; and $t_{1/2}$ Streptavidin=11.2 and 9.6 min, respectively). (E-F) Measurements of current (μA) in target concentration (M) are shown and represent the dose-response curves of antibody (E) and streptavidin (F). Experiments were performed in 50 mM $NaH_2PO_4$, 150 mM NaCl, pH 7.0. Values represent the mean current of triplicate measurement±standard deviation. The error bars represent the typical standard deviation obtained when working with three electrodes and are dominated by inter-electrode variability.

FIG. 13 illustrates an embodiment of the system for detecting small molecules using an aptamer as a macromolecular entity (via a structure-switching mechanism or a competition assay). In this embodiment, an aptamer displaying high affinity and high specificity for a molecular target (usually a small molecule or a protein) is bound to the signaling oligonucleotide via a short complementary sequence (considered as a moiety for binding a macromolecular entity) located on the signaling oligonucleotide. (A) In presence of the target (top), the aptamer prefers to adopt its binding competent conformation, which displays a lower affinity for the complementary signaling oligonucleotide. The free signaling oligonucleotide therefore produces less steric hindrance near the sensor surface, which results in an increase of hybridization efficiency between the signaling and anchoring oligonucleotides and ultimately an increase in the signal from the sensor. In absence of the target (bottom), the signaling oligonucleotide, in complex with the relatively large aptamer creates steric hindrance near the sensor surface thus leading to low electrochemical signal. (B) Representation of the current measured in the presence or absence of the target in function of time when an aptamer is used as the macromolecular entity.

DETAILED DESCRIPTION

Figure 3A:
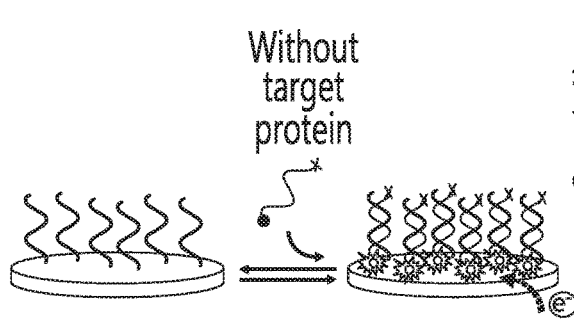
FIG. 3 illustrates the dose response curve of eSHHA with increasing concentration of signaling oligonucleotides. In order to optimize the sensitivity of eSHHA, the minimal amount of signaling DNA oligonucleotide that is needed to saturate all the anchoring oligonucleotides at the surface of the electrode was first determined. (A) Schematic representation of the system used. The system used is similar to the one illustrated on FIG. 2 but it does not contain the macromolecular target (protein). (B) The dose response curves (current in μA in function of signaling oligonucleotide concentration (M)) of three different hand-made electrodes display similar cooperative curves that become saturated at around 100 nM of signaling oligonucleotides. A reproducibility of 9.5% is typically obtained with these electrodes. All the experiments performed in the Example were done using a signaling oligonucleotide concentration of 100 nM, thus insuring a high, robust electrochemical signal in absence of targeted protein. This signaling oligonucleotide concentration also insures that a precise protein quantification is observed between 1 nM and 100 nM (the expected saturation point). Without wishing to be bound to theory, it is expected that a higher signaling oligonucleotide concentration would simply shift the protein's binding curve to arbitrarily higher concentration since more proteins would be needed to saturate all signaling oligonucleotide. It was noted that the electrochemical currents obtained at saturation points are 40% higher than current obtained for single point measurements in absence of macromolecular targets in the results obtained in the Example. These higher currents are likely attributable to the fact that in this experiment, hybridization of signaling DNA took place over a wide time period (5 hr) by sequentially adding more and more signaling DNA after waiting up to 35 min following each addition. Electrodes with a smaller diameter are expected to be saturated at lower concentration of signaling DNA oligonucleotide since these contain less anchoring oligonucleotides.

In accordance with the present disclosure, there is provided systems as well as associated methods for the detection, and optionally the semi-quantification or the quantification, of a target in a sample based on the use of steric hindrance created by the binding of a macromolecular entity with a set of at least two distinct oligonucleotides (e.g., an anchoring and a signaling oligonucleotides) described herewith. As shown herein, the system is designed to allow the generation of a signal when the anchoring/signaling oligonucleotides are hybridized with one another and to modulate such signal in the presence or absence of the target. The system can also allow, in some embodiment, the quantification of such signal modulation to assess the amount of the target in the sample.

In some embodiments, the systems and methods can be designed such as to allow the detection of a single target or a combination of different targets. As it will be shown herein, the systems and methods do not necessarily rely on the ability of the targets to bind nucleic acid molecules or to bind to at least two target-binding moieties simultaneously to allow their detection/quantification. In embodiments, the system and methods do not require the amplification of the targets prior to their detection/quantification. In some embodiments, the systems and methods can be designed to allow detection/quantification in complex untreated mixtures, such as whole blood or food.

Detections Systems and Associated Kits

The detection system described herein comprises at least three components: an anchoring oligonucleotide (also referred to as a capture oligonucleotide), a substrate (to which the anchoring oligonucleotide is associated) and a unimolecular or modular signaling oligonucleotide (capable of hybridizing/base-pairing with the anchoring oligonucleotide). In some embodiment, when the target is not a macromolecular entity or capable of binding to the signaling oligonucleotide, the detection system can also comprise a macromolecular entity (capable of binding to the signaling oligonucleotide). The detection system includes at least two separate oligonucleotides that are capable of associating with each other in the presence and in the absence of the macromolecular entity as well as in the presence and in the absence of the target. The base-pairing or hybridization efficiency between of the anchoring and the signaling oligonucleotide allows the generation of a quantifiable signal. However, because the anchoring oligonucleotide is associated at one of its end to the surface of the substrate at a specific density, the association of the macromolecular entity with the signaling oligonucleotides creates steric hindrance and modulates the ability of other signaling oligonucleotides to associated with adjacent anchoring oligonucleotides. Ultimately, the signal associated with the hybridization between the anchoring and the signaling oligonucleotides is modulated. This modulation allows the detection, and in some embodiment, the quantification of the target in the sample.

The system described herein is for the detection, and optionally the quantification, of one or more targets in a sample. In the context of the present disclosure, a sample is mixture (either already in a liquid or capable of being provided as in a liquid form) suspected of containing the target or the combination of targets of interest. The sample can be a solution or a suspension. The sample can be processed into a solution or a suspension. The sample can be a biological sample. Exemplary biological samples include, but are not limited to, bodily fluids (e.g., blood, urine, gastro-intestinal juice, interstitial fluid, lachrymal fluid, sweat, saliva, stools, sputum, pus, cerebrospinal fluid, semen, prostatic fluid, milk, nipple aspirate fluid, lachrymal fluid, perspiration), tissues (swabs (e.g., cheek swabs), tissue biopsy), fractionated bodily fluids (serum, plasma, etc.), cell extracts (e.g., cytoplasmic membrane, mitochondrial extract, nuclear extracts, etc.), cell suspensions, secretions as well as cultures of such biological samples. The sample can be an environmental sample, such as, for example, a water, a gas sample or a soil sample. The sample can also be a food sample.

The detection system is configured into at least two detachable and base-pairable/hybridizable elements: a substrate associated with anchoring oligonucleotides (capable of hybridizing with the signaling oligonucleotide) and signaling oligonucleotides (capable of hybridizing with the anchoring oligonucleotide). The substrate is associated with at least two (and, in an embodiment, a plurality of) anchoring oligonucleotides at two (and in an embodiment a plurality of) discrete and adjacent positions. The system comprises at least two (and in an embodiment a plurality of) signaling oligonucleotide. The anchoring oligonucleotides are configured such that they are associated at one of their end to the surface of the substrate and, at their other end, have a free end (e.g., not associated directly with the surface of the substrate). When the signaling oligonucleotide is unimolecular, it is designed to bear, at one end, a moiety for binding a macromolecular entity and, at the other end, a reporter moiety. When the signaling oligonucleotide is modular, it is designed to include in a first element a moiety for binding a macromolecular entity (labeling element) and a second element a reporter moiety (adaptor element). The anchoring oligonucleotides and the signaling oligonucleotides are configured for hybridizing with one another and to localize the reporter moiety of the signaling oligonucleotide in the vicinity of the surface of the substrate. When the macromolecular entity is not capable of forming a complex with the signaling oligonucleotide (either because the target is not present in the sample or because the macromolecular entity forms a complex with the target), the anchoring and signaling oligonucleotides hybridized together at the two (and, in an embodiment, at a plurality of) discrete and adjacent positions on the substrate where the anchoring oligonucleotides are located. In this embodiment, the reporter moiety of each of the bond signaling oligonucleotides, in collaboration with the surface of the substrate, modulates (in an embodiment, generates) the production of a signal which can be detected and quantified. When the macromolecular entity forms a complex with the signaling oligonucleotide (because the target is absent from the sample), a complex is formed between at least one anchoring oligonucleotide, at least one signaling oligonucleotide and the macromolecular entity and the presence of such complex creates steric hindrance at one location on the substrate thereby limiting or preventing the hybridization between another adjacent anchoring oligonucleotide and a further signaling oligonucleotide (associated or not with a macromolecular entity). The absence of such hybridizing at the adjacent position modulates (e.g., reduces) the number of reporter moiety brought to the surface of the substrate. Such signal can be detected and quantified.

The system presented herewith is used for the detection of a target. As used in the context of the present disclosure, the "target" maybe any molecule of interest which is suspected to be present in a sample to be analysed and is capable of binding (in an embodiment specifically) to a macromolecular entity or to the signaling oligonucleotide. In the context of the present disclosure, the expression "specific binding" or "specifically bind" refers to the interaction between two elements in a manner that is determinative of the presence of the elements in the presence or absence of a heterogeneous population of molecules that may include nucleic acids, proteins, and other biological molecules. For example, under designated conditions, a target binds to a particular macromolecular entity and does not bind in a significant manner to other molecules in the sample. In some embodiments (when the target is considered to be a macromolecular entity), "specific binding" of the target to the signaling oligonucleotide results in steric hindrance at the surface of the substrate which ultimately creates a detectable signal or a detectable change in a signal. In other embodiments, "specific binding" of a macromolecular entity to the target inhibits steric hindrance at the surface of the substrate which ultimately creates a detectable signal or a detectable change in a signal.

An embodiment of the system is presented in FIG. 1A. In this embodiment, the system was designed to detect, and ultimately quantify, the presence of a target antibody. In this embodiment, the target is a macromolecular entity and is capable of binding the signaling oligonucleotide (because the latter contains an epitope recognized by the antibody as a moiety for binding the macromolecular entity). Those skilled in the art would understand that other targets being macromolecular entities and capable of binding to signaling oligonucleotides (via the same or a different moiety) can be detected with this embodiment of the system. In the system illustrated on FIG. 1A, a substrate (such as a gold electrode) 010 is provided and bears on its surface a plurality of anchoring oligonucleotides 020. The anchoring oligonucleotides 020 all have the same nucleic acid sequence and are located at a plurality of discrete locations on the substrate 010. The anchoring oligonucleotides 020 are attached to the surface of the substrate 010 via one of their end (in some embodiment, their first end) while the other end is not attached directly to the surface of the substrate 010 (e.g., it is considered to be a "free" end). The signaling oligonucleotides 030 of the system have three distinct segments (in this embodiment, the signaling oligonucleotide is unimolecular and its segments are conveniently covalently linked with one another): a nucleic acid molecule 032 which is capable of hybridizing with the anchoring oligonucleotide 020; a moiety 031 for binding a macromolecule (□, also referred to as a small recognition element or as a moiety for binding the macromolecular entity) and a moiety 033 acting as a reporter (●, in some embodiments referred to as a redox label or as a reporter moiety). The nucleic acid molecules 032 of the signaling oligonucleotides 030 all have the same nucleic acid sequence and are capable of hybridizing with the anchoring oligonucleotide. In the absence of the antibody target 040 (top panel), the signaling oligonucleotides 030 are free to interact with the anchoring oligonucleotides 020 and create a plurality of nucleic acid duplexes 050 on the surface of the substrate 010. The signaling oligonucleotides are designed such that the reporter moiety 033 is located in the vicinity of the substrate 010 surface upon the formation of the duplexes 050. As such, a signal (such as an electrochemical signal (current for example)) is generated upon the formation of the duplexes 050. On the other hand, in the presence of the antibody target 040 (bottom panel), the signaling oligonucleotides 030 form complexes 055 with the target and interact with the anchoring oligonucleotides 020 to form a plurality of complexes 060 on the surface of the substrate 010. The complexes 060 contain an anchoring oligonucleotide 020, a signaling oligonucleotide 030 (based-paired to the anchoring oligonucleotide) and the target macromolecular antibody 040. The presence of the complexes 060 at the surface of the substrate 010 allows the generation of a signal (such as an electrochemical signal (current for example)) but prevents the formation of another complex 060 at an adjacent position 011 on the surface of the substrate 010. As such, in such embodiment, in the presence of a target antibody, less signal is generated from the substrate and this reduction in signal allows for the detection and optionally quantification of the target antibody in the sample being tested (see FIG. 1B).

In the embodiment presented in FIG. 1, the target is capable of creating steric hindrance at an adjacent position on the surface of a substrate when it forms a complex with the anchoring oligonucleotide and the signaling oligonucleotide and is also capable of specifically binding a moiety located at one of the end of the signaling oligonucleotide. In an embodiment, the target can have an average molecular weight of at least 10 kDa, at least 20 kDa, at least 30 kDa, at least 40 kDa, at least 50 kDa, at least 60 kDa, at least 70 kDa, at least 80 kDa, at least 90 kDa or at least 100 kDa. The target can be antibody (IgA, IgE, IgG, IgM, IgD), a single-chain antibody or an antibody fragment (Fab' fragment for example). The target can be a cell (such as, eukaryotic cell (e.g., an immune cell) or a prokaryotic cell (e.g., a bacteria)) or a cellular fragment (such as, for example, an erythrocyte or a platelet). The target can be an infectious agent, such as, for example, a prokatyotic cell (e.g., a bacteria), a fungal cell (e.g., a yeast or a mold), a virus or a prion. The target can also be a polymeric molecule (e.g., a polynucleotide molecule (DNA—(including cDNA and DNA fragments) and RNA-based (including mRNA, miRNA, tRNA, siRNA), a polypeptide molecule or a carbohydrate (e.g., a lectin) for example) or can be a monomeric molecule (e.g., a lipid for example). When the macromolecule is a polynucleotide molecule, it comprises at least 20, 30, 40, 50 or at least 100 nucleic acid bases. Exemplary polypeptides/proteins include, but are not limited to, antibodies, cellular receptors, secreted polypeptides, immuno-modulatory polypeptides (interleukins, interferons), hormones (such as growth factors), coagulation factors, DNA-binding polypeptides (such as transcription factors), etc. The target can be a single molecule, combination of two or more molecules (e.g., a glycosylated antibody for example) or an aggregation of two or more molecules. The target can be a naturally-occurring molecule or a synthetic (e.g., man-made) molecule.

In another embodiment (such as the one presented in FIGS. 11 to 13), the target itself does not create steric hindrance at an adjacent position on the surface of a substrate because it is not capable of specifically binding a moiety located at one of the end of the signaling oligonucleotide. In such embodiment, the system further comprises a macromolecular entity capable of binding to the target and to the signaling oligonucleotide In an embodiment, the macromolecular entity has an average molecular weight of at least 10 kDa, at least 20 kDa, at least 30 kDa, at least 40 kDa, at least 50 kDa, at least 60 kDa, at least 70 kDa, at least 80 kDa, at least 90 kDa or at least 100 kDa. The macromolecular entity can be an antibody (IgA, IgE, IgG, IgM, IgD), a single-chain antibody or an antibody fragment (Fab' fragment for example). The macromolecular entity can be a cell (such as, eukaryotic cell (e.g., an immune cell)) or a cellular fragment (such as, for example, an erythrocyte or a platelet) The macromolecular entity can be an infectious agent, such as, for example, a prokatyotic cell (e.g., a bacteria), a fungal cell (e.g., a yeast or a mold), a virus or a prion. The macromolecular entity can also be a polymeric molecule (e.g., a polynucleotide molecule (DNA—(including cDNA and DNA fragments) and RNA-based (including mRNA, miRNA, tRNA, siRNA), a polypeptide molecule or a carbohydrate (e.g., a lectin) for example) or can be a monomeric molecule (e.g., a lipid for example). When the macromolecular entity is a polynucleotide molecule, it comprises at least 20, 30, 40, 50 or at least 100 nucleic acid bases. Exemplary polypeptides include, but are not limited to, antibodies, cellular receptors, secreted polypeptides, immuno-modulatory polypeptides (interleukins, interferons), hormones (such as growth factors), coagulation factors, DNA-binding polypeptides (such as transcription factors), etc. The macromolecular entity can be a single molecule, combination of two or more molecules (e.g., a glycosylated antibody for example) or an aggregation of two or more molecules. The target can be a naturally-occurring molecule or a synthetic (e.g., man-made) molecule.

Figure 11A:
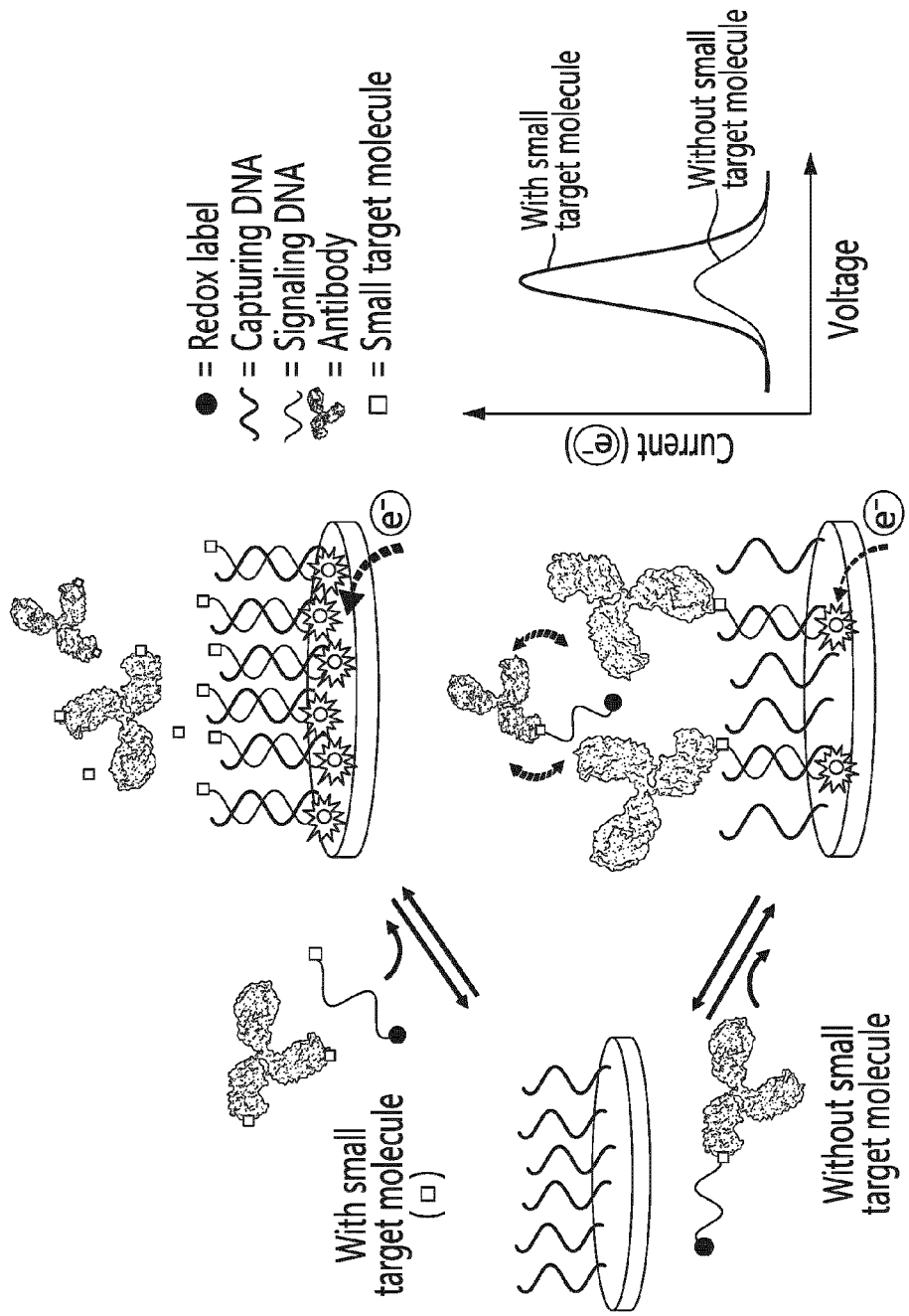
FIG. 11 illustrates an embodiment of the system designed for the detection of small molecule targets (e.g., a competitive assay). (A) In the presence of the small target molecule (top panel), the later binds to a macromolecular entity (e.g., antibodies specifically recognizing the small molecule target) that has been added to the sample. The binding of the target to the macromolecular entity prevents the macromolecular entity from binding to the signaling oligonucleotide. Thus, the signaling oligonucleotide will bind to most of the anchoring oligonucleotides on the sensor's surface thus generating a large signal by bringing many signaling moieties near the sensor's head (bold line in the left panel). In the absence of the small target molecule (lower panel), the macromolecular entity (e.g., antibodies) will bind to the signaling oligonucleotide forming a complex which will reduce the number of signaling oligonucleotide that will attach on the electrode surface due to steric hindrance (regular line in the left panel. (B-C) This embodiment was tested directly in whole blood for the detection of digoxin using anti-digoxin antibody (50 nM) and 100 nM of digoxigenin-labeled signaling oligonucleotide. Results are shown for the measurement of the current (in µA) in function of time (B) or concentration of digoxigenin (C).
Figure 11C:
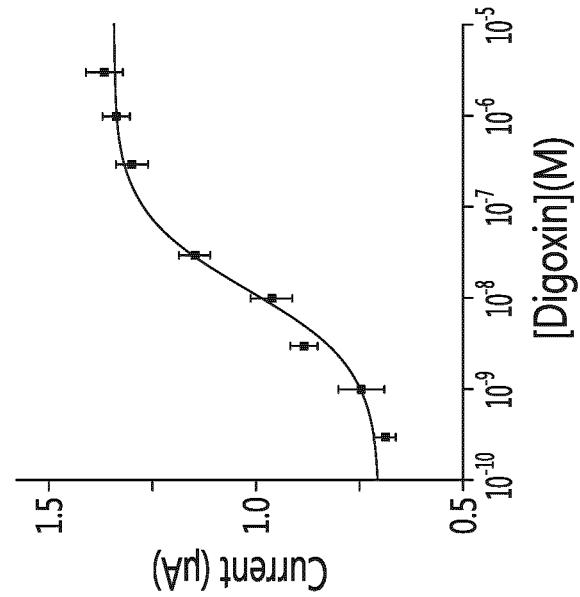
Figure 11B:
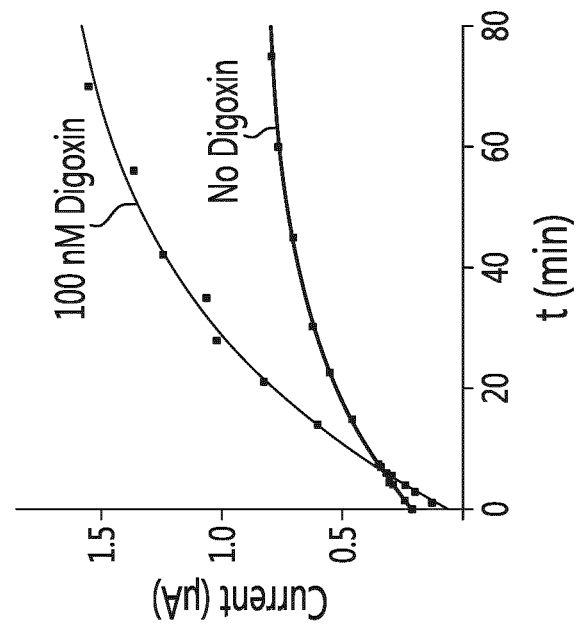

In the embodiment presented in FIG. 11, the target can be a small molecule. In the context of the present disclosure, the small molecule binds to a macromolecule entity (and antibody, a lectin or an aptamer for example) which is no longer capable of binding to the signaling oligonucleotide to create steric hindrance at an adjacent position. In such embodiment of the system, the small molecule can be attached to one of the end of the signaling oligonucleotide. In another embodiment of the system, the moiety for binding the macromolecular entity is not the target itself, but another moiety capable of binding to the macromolecular entity, albeit with a lesser affinity than the target itself. In such embodiments, the moiety has an average molecular weight of less than 10 kDa, less than 5 kDa, less than 4 kDa, less than 3 kDa, less than 2 kDa or less than 1 kDa. The moiety can also be a polymeric molecule (e.g., a polynucleotide molecule (DNA—(including cDNA and DNA fragments) and RNA-based (including mRNA, miRNA, tRNA, siRNA), a peptide molecule or a carbohydrate for example) or can be a monomeric molecule (e.g., a lipid for example). When the moiety is a polynucleotide, it comprises no more than 50 nucleic acid bases. When the moiety is a peptide, it comprises no more than 70 amino acid residues. When the moiety is the small molecule target, it be can be, for example, a naturally-occurring molecule or a synthetic (e.g., man-made) molecule, such as a drug, a metabolite, a contaminants, a metal, etc.

As indicated above, when target is not a macromolecular entity or capable of binding to the signaling oligonucleotide and is being detected, the system further comprises a macromolecular entity which is added to the sample to be analysed. This macromolecular entity (an antibody for example) is capable of specifically binding to the target. The signaling oligonucleotide is configured such that it can specifically bind the macromolecular entity only in the absence of the target. So, in the presence of the target, the macromolecular entity preferably binds the target, does not bind the signaling oligonucleotide, the latter being available for hybridizing with the anchoring oligonucleotide. However, in the absence of the target, the macromolecular entity bind the signaling oligonucleotide and creates steric hindrance at the surface of the substrate. In some embodiments, to improve the limit of detection of the assay, it may be important that the macromolecular entity displays more affinity for the free small molecule target than for moiety for binding the macromolecular entity.

Figure 12:
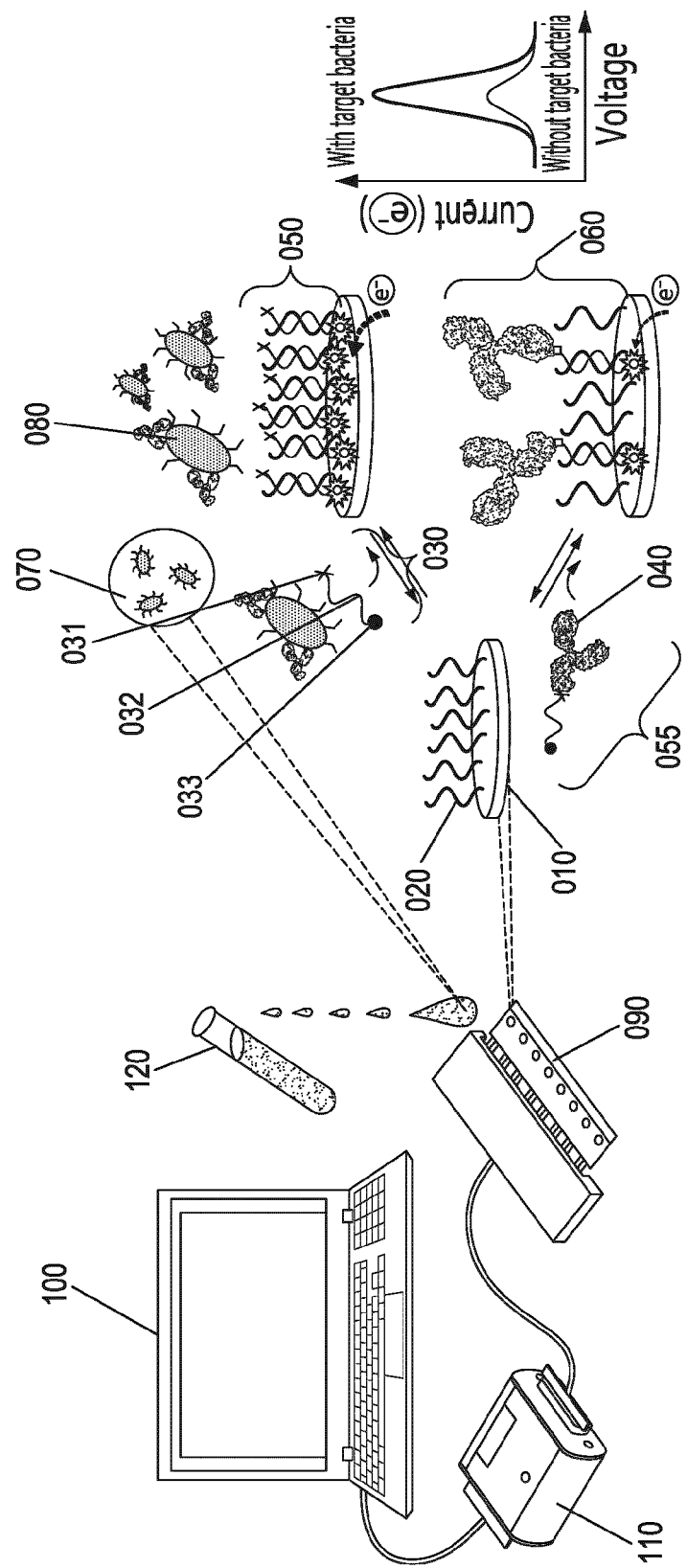
FIG. 12 illustrates an embodiment of the system similar to FIG. 11 but for detecting a target bacteria. In this embodiment, the system is designed so that the bacteria will sequester its corresponding anti-antibodies and these later will no longer be available to bind the signaling oligonucleotide. The presence of a specific bacteria strain can therefore be detected through the generation of high electrochemical current.

Another embodiment of the system is presented in FIG. 12. In this embodiment, the system was designed to detect, and ultimately quantify, the presence of a target bacteria (which can be resistant to one or more antibiotic or present in food or water). Even though the target bacteria is considered a macromolecule, since it is not capable of binding to the signaling oligonucleotide, a further macromolecular entity (an antibody specific for the bacteria) is used. In the embodiment shown on FIG. 12, the signaling oligonucleotide bears an epitope recognized by the antibody as a moiety for binding the macromolecular entity. Those skilled in the art would understand that other targets (such as viruses, metabolites, drugs, etc.) which may or may not be considered macromolecules can be detected with this embodiment of the system. In the system illustrated in FIG. 12, a substrate (such as a gold electrode) 010 is provided and bears on its surface a plurality of anchoring oligonucleotides 020. The anchoring oligonucleotides 020 all have the same nucleic acid sequence and are located at a plurality of discrete locations on the substrate 010. The anchoring oligonucleotides 020 are attached to the surface of the substrate 010 via one of their end (in some embodiment, their first end) while the other end is not attached directly to the surface of the substrate 010 (e.g., it is considered to be a "free" end). The signaling oligonucleotides 030 have three distinct moieties (in this embodiment, the signaling oligonucleotide is unimolecular and its elements conveniently covalently linked with one another): a nucleic acid molecule 032 which is capable of hybridizing with the anchoring oligonucleotide 020; a moiety 031 for binding the antibody (X, which, in this embodiment, is an epitope specifically recognized by the antibody and present on the target bacteria) and a moiety 033 acting as a reporter (●, in some embodiments referred to as a redox label). The nucleic acid molecules 032 of the signaling oligonucleotides 030 all have the same nucleic acid sequence. In the presence of the target bacteria 070 (top panel), the antibodies 040 specifically bind the bacteria 070 to form an antibody-bacteria complex 080. The formation of the antibody-bacteria complexes allows the signaling oligonucleotides 030 to freely interact with the anchoring oligonucleotides 020 at the discrete locations of the substrate 010 and create a plurality of duplexes 050 on the surface of the substrate 010. The signaling oligonucleotides are designed such that the reporter moiety 033 is located in the vicinity of the substrate 010 surface upon the formation of the duplexes 050. As such, a signal (such as an electrochemical signal (current for example)) is generated upon the formation of the duplexes 050. In the absence of the target bacteria 070 (bottom panel), the signaling oligonucleotides 030 associate with the antibody 040 to form a complex 055 and interact with the anchoring oligonucleotides 020 to create a plurality of complexes 060 on the surface of the substrate 010. The complexes 060 contain an anchoring oligonucleotide 020, a signaling oligonucleotide 030 (hybridized to the anchoring oligonucleotide) and the antibody 040. The presence of the complexes 060 at the surface of the substrate 010 allows the generation of a signal (such as an electrochemical signal (current for example)) but prevents the formation of another nucleic acid complexes 060 at an adjacent position 011 on the surface of the substrate 010. As such, in such embodiment, in the absence of the target bacteria, less signal is generated and this reduction in signal allows for the detection and optionally quantification of the target bacteria in the sample being tested (see panel on bottom left of the figure). In the embodiment illustrated on FIG. 12, the system can be designed as a portable inexpensive sensor 090 (which can be a multiplex sensor) attached to a computer 100 via a potensiostat 110. In the embodiment illustrated on FIG. 12, the system can be located in a sensor 090. A food sample or a bacterial culture 120 of a food sample can be placed in contact with the sensor 090 to make the determination of the presence or absence of the target bacteria. The sensor 090 can be linked to a computer 100 via a potensiostat 110.

Also contemplated herein is the use of an aptamer as a macromolecular entity for detecting a target that is not capable of binding to the signaling oligonucleotide. An illustration of such embodiment is provided in FIG. 13. In this figure, the signaling oligonucleotide has a, as a moiety 033 for binding a macromolecular entity, a nucleic acid sequence (aptamer-binding sequence). In the embodiment shown on FIG. 13, the signaling oligonucleotide is made of DNA. The aptamer-binding sequence is sufficiently long to bind specifically to the aptamer (at least 5, 6, 7, 8 or 9 nucleotide-long) and sufficiently short (at most 20, 19, 18, 17, 16 or 15 nucleotide-long) in order to allow the aptamer to dissociate from this signaling oligonucleotide upon binding to its target. In the presence of the target (FIG. 13A, top), the aptamer preferentially binds to it, thereby releasing the signaling oligonucleotide which is then free to interact with the anchoring oligonucleotides at various adjacent positions to create a signal (FIG. 13B, dashed line). In the absence of the target (FIG. 13A, bottom), the aptamer remains associated with the signaling oligonucleotides which can also associate with the anchoring oligonucleotide, albeit at a lower density than in the presence of the target because of the steric hindrance caused by the presence of the aptamer at the surface of the substrate. This creates a signal which is much lower than when the target is present (FIG. 13B, regular line).

In the context of the present disclosure, the aptamer must be capable of creating steric hindrance at the surface of the substrate when it is associated with the anchoring oligonucleotide via the signaling oligonucleotide. Aptamers are usually between 20 and 90 nucleic acid-long. If the length or the tri-dimensional configuration of the aptamer does not create sufficient steric hindrance on the surface of the substrate, it is contemplated herewith to modify the aptamer to include additional nucleic acid bases which are not involved in hybridizing with the signaling oligonucleotide or the binding to the target. For example a poly-T tail can be added, either at the 3'-terminus or 5'-terminus of the aptamer to increase its size (and ultimately increase its ability to create hindrance at the surface of the substrate).

Still in the context of the present disclosure, the aptamer must be capable of hybridizing to the signaling oligonucleotide. If the aptamer is not capable of hybridizing with the signaling oligonucleotide, it is contemplated herewith to modify the aptamer to include additional nucleic acid bases (either at the 3'-terminus or the 5'-terminus) which are not involved in hybridizing with binding to the target.

In certain embodiments, the detection system described herein is capable of specifically identifying nanomolar or picomolar concentrations of targets in a sample. In some embodiments, the system has a dynamic range of at least 10, 20, 30, 40, 50, 60, 70 or 80.

For example, in embodiments in which the signaling oligonucleotide is unimolecular and used at a concentration of 100 nM, the system can detect a target having a concentration ranging from 1 nM to 1 µM, such as from 1 nM to 750 nM, including from 1 nM to 500 nM, or from 1 nM to 250 nM, for instance from 1 nM to 100 nM or from 2 nM to 160 nM.

In an embodiment, the oligonucleotides concentration and density, and especially the density of the anchoring oligonucleotide can be dynamically modulated to detect the target to take into considered the size of the target/macromolecular entity as well as the size of the substrate. For example, when an antibody (having an average size between 10 and 15 nm, such as 12 nm) is used as a target or as a macromolecular entity, the anchoring oligonucleotides can be anchored at discrete locations spaced between about 2 to 5 nm apart, between about 3 to 5 nm apart or between 4 to 5 nm apart. In an embodiment, when an antibody is used as a target or as a macromolecular entity, the anchoring oligonucleotides can be anchored at discrete locations spaced about 4 nm apart. In an embodiment, the complex between the hybridized signaling and the anchoring oligonucleotide (in the absence of the macromolecular entity) form a complex having a mean diameter of about 2 nm. In such embodiment, the spacing between the anchoring oligonucleotides is at least 2 nm, and in some embodiments at least about 3 nm. In some embodiments, the spacing between the anchoring oligonucleotides on the surface of the substrate is between about 2 nm and about 3 nm.

In a certain embodiment, the anchoring oligonucleotide surface density (i.e., the number of anchoring oligonucleotide as mole per unit area of the substrate surface, $N_{tot}$) can be determined using a previously established relationship with peak current as described in O'Connor et al. (1999) and Idili et al. (2014):

$$I_{peak}(E_0) = 2nfFN_{tot} \frac{\sinh(nFE_{ac}/RT)}{\cosh(nFE_{ac}/RT) + 1}$$

where $I_{peak}$ ($E_0$) is the average AC peak current in a voltammogram, n is the number of electrons transferred per redox event (with our MB label n=2), F is the Faraday current, R is the universal gas constant, T is the temperature, $E_{ac}$ is the amplitude, and f is the frequency of the applied voltage perturbation. In an embodiment, it was assumed that each anchoring oligonucleotide could hybridize to a signaling oligonucleotide and that electron transfer only takes place between reporter moiety and the substrate surface upon binding of the signaling oligonucleotide (assuming a perfect electron transfer for each oligonucleotide bound reporter moiety). Dividing $N_{tot}$ by the geometric surface area of the substrate resulted in the anchoring oligonucleotide surface density in terms of moles/cm². Considering a circle area around each oligonucleotide associated to the substrate surface, this area was estimated from reversing the value of density (oligonucleotides/cm²), and consequently the distance was then calculated from the diameter of this circle area.

One of the component of the detection system described herein is an anchoring oligonucleotide. In the detection system described herein, the anchoring oligonucleotide is capable of localizing signaling oligonucleotide near the surface of the substrate at least two adjacent positions on the substrate. Still in the detection system described herein, the anchoring oligonucleotide is not free to diffuse in solution, it associated (and, in an embodiment, covalently associated) to the surface of the substrate.

In the context of the present disclosure, the anchoring oligonucleotide is an oligonucleotide, preferably single-oligonucleotideed and linear, which is associated at one of its end (referred to the "first" end) to the surface of the substrate. It is contemplated that the anchoring oligonucleotide be associated to the surface of the substrate either via a terminal nucleic acid base (e.g., its 5' or 3' nucleic acid terminus) or via an internal nucleic acid base, preferably located within the five nucleic acid bases adjacent to the 5' or 3' nucleic acid terminus of the anchoring nucleotide. In an embodiment, the anchoring oligonucleotide is attached via its first end in a covalent manner to the surface of the substrate. The anchoring oligonucleotide can be associated directly to surface of the substrate or, alternatively, can be associated to the surface of the substrate through the use of a linker. The other end of the anchoring oligonucleotide (referred to as the "second" end) is considered "free" because it is not attached directly to the surface of the substrate. The anchoring oligonucleotide is configured such that a region (referred to as a "complementary region") is exposed and is free to hybridiz with the signaling oligonucleotide.

Figure 14B:
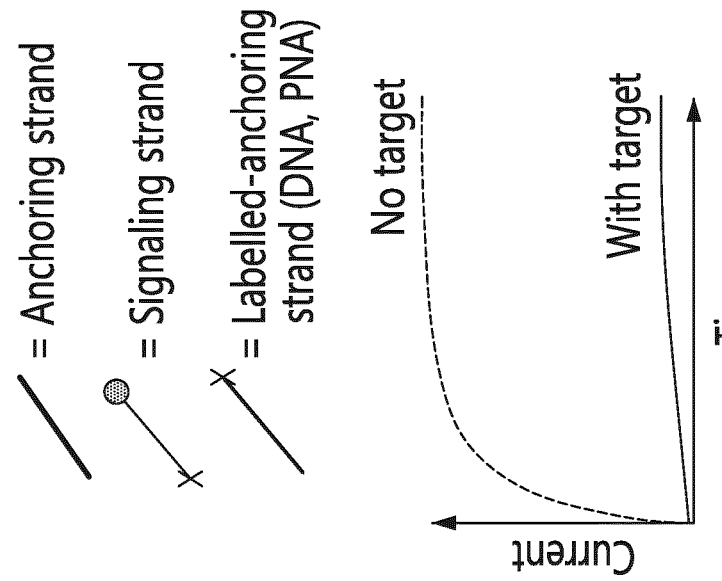
FIG. 14 illustrates an embodiment of the present disclosure for increasing current reduction when the target is a macromolecule (an antibody for example). In this embodiment, a moiety for binding the macromolecule can also be added at the free end of a certain (specific) fraction of the anchoring oligonucleotides at the surface of the electrode. (A) In the presence of the target macromolecule (bottom), the later creates a thin macromolecule film at the surface of the sensor (via its attachment to the anchoring oligonucleotide) which contributes in enhancing steric hindrance and thus reduce, even more, the efficiency of hybridization between the macromolecule bound-signaling oligonucleotide and the anchoring oligonucleotide. (B) Representation of the current measured in the presence or absence of the target in function of time when a moiety for binding a macromolecular entity is added to the free end of the anchoring oligonucleotide.
Figure 14A:
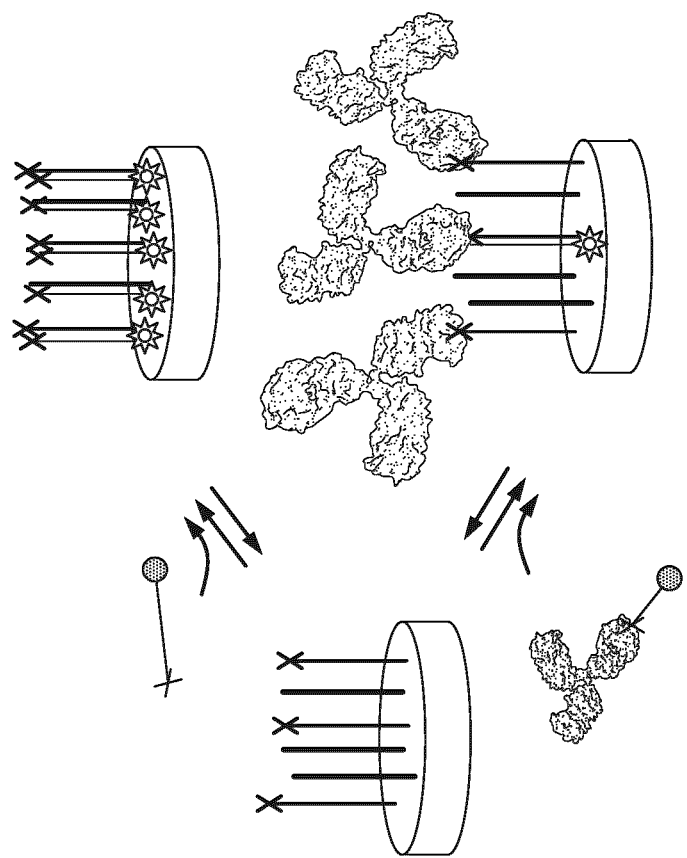

In an embodiment of the system (such as the one illustrated at FIG. 14), a portion of the anchoring oligonucleotides can be associated (via their "free" end) to a moiety for binding a macromolecular entity. This embodiment is especially useful when the target is a macromolecular entity and there is a need for amplifying the gain in the absence/presence of the target. In the embodiment illustrated at FIG. 14, 50% of the anchoring oligonucleotides of the system bear, at their "free" end, a moiety for binding the macromolecular entity (X), whereas the other 50% of the anchoring oligonucleotides. In the absence of the target (top), the anchoring and the signaling oligonucleotides can interact at a plurality of adjacent positions because there is no steric hindrance created on the surface of the sensor. In the presence of the target (bottom), some of the macromolecular entities associate with the anchoring oligonucleotide and create a "film" of steric hindrance at the surface of the sensor. Other molecular entities associate with the signaling oligonucleotide and eventually can form a complex at the surface of a sensor to provide a signal. In this embodiment of the system, at least 10, 20, 30, 40, 50, 60, 70, 80 or 90% of the anchoring oligonucleotides can bear a moiety for binding a macromolecular entity. Still in another embodiment of the system, no more than 90, 80, 70, 60, 50, 40, 30, 20 or 10% of the anchoring oligonucleotides can bear a moiety for binding a macromolecular entity.

In embodiments of the system in which the anchoring oligonucleotide is associated to the surface of the substrate indirectly via a linker, it is contemplated that the linker can be any linker which will allow the positioning of the reporter moiety of the signaling oligonucleotide close to the surface of the substrate upon the hybridizing of the anchoring oligonucleotide with the signaling oligonucleotide. In an embodiment, the linker moiety may include 1 to 25 carbon atoms, such as 2 to 20 carbon atoms, including 5 to 15 carbon atoms. Exemplary embodiments of the linker include, but are not limited to, alkyl, preferably a lower straight-chain alkyl (e.g., $C_1$ to $C_{10}$) and even more preferably a $C_1$-$C_6$ alkyl. In some embodiments, the linker is a $C_6$ straight-chain alkyl.

The anchoring oligonucleotide is composed of any combination of known natural or synthetic nucleic acid bases and its backbone can be modified from naturally-occurring backbones. Naturally-occurring oligonucleotides contain phosphodiester bonds and synthetic oligonucleotides comprising nucleic acid analogs may have alternate backbones, comprising, for example, phosphoramide, phosphorothioate, phosphorodithioate, O-methylphosphoroamidite linkages and peptide nucleic acid backbones and linkages. Other analog nucleic acids analogs include those with positive backbones, non-ionic backbones, and non-ribose backbones. Nucleic acids bases containing one or more carbocyclic sugars are also included within the definition of contemplated nucleic acid bases.

The anchoring oligonucleotide generally has a total length between 10 and 30 nucleic acid bases. The length and composition (GC and AT content) of the anchoring oligonucleotide is designed in order to achieve a sufficiently good affinity between the anchoring and signaling oligonucleotides (for example, a $K_D$ of at least 10 nM). The anchoring oligonucleotide can have a total length of at least 10, 11, 12, 13, 14, 15, 16, 17, 18, 19, 20, 21, 22, 23, 24, 25, 26, 27, 28, 29 or 30 nucleic acid bases and/or a total length of no more than 30, 29, 28, 27, 26, 25, 24, 23, 22, 21, 20, 19, 18, 17, 16, 15, 14, 13, 12, 11 or 10 nucleic acid bases. The anchoring oligonucleotide also comprises a region designed for hybridizing to the signaling oligonucleotide (referred to a complementary region). The complementary region is at least 10, 11, 12, 13, 14, 15, 16 or 17 and/or no more than 17, 16, 15, 14, 13, 12, 11 or 10 contiguous nucleic acid bases long. The level of identity between the complementary region of the anchoring oligonucleotide and the corresponding complementary region of the signaling oligonucleotide is at least 80%, 85%, 90%, 91%, 92%, 93%, 94%, 95%, 96%, 97%, 98%, 99% or 100%. In one embodiment, the entire length of the anchoring oligonucleotide is complementary to the a corresponding complementary region of the signaling oligonucleotide. In another embodiment, the anchoring oligonucleotide comprises additional nucleic acid bases which are not involved into the hybridizing with the signaling oligonucleotide (located 3' and/or 5' with respect to the complementary region).

Another component of the detection system described herein is a substrate. In the context of the present disclosure, the substrate provides a surface for associating with at least two anchoring oligonucleotides to prevent them from freely diffusing in solution/suspension. In close proximity to the reporter moiety of signaling oligonucleotide, the surface of the substrate is also capable of creating, modulating or conducting a signal upon the hybridizing of the signaling oligonucleotide with the anchoring oligonucleotide. For example, the surface of the substrate can be a fluorescent one and the reporter moiety on the signaling oligonucleotide can be a quencher moiety capable of limiting the fluorescence associated with the surface of the substrate. In such embodiment, upon the hybridizing of the anchoring oligonucleotide with the signaling oligonucleotide, the quencher moiety comes into close proximity with the fluorescent surface of the substrate and create a modulation (e.g., reduction) in fluorescence, which can be detected and quantified. In another example, the substrate is a metallic electrode (such as a gold electrode) and the reporter moiety is a redox-reporter (methylene blue for example). In such example, upon the hybridizing of the anchoring oligonucleotide with the signaling oligonucleotide, the redox-moiety will come into close contact with the gold electrode and create a modulation in the current which be detected and optionally quantified.

The anchoring oligonucleotides are associated on the surface of the substrate at various discrete positions. The anchoring oligonucleotides are configured on the surface of the substrate at a density which would prevent the hybridizing between two adjacent positions on the substrate when, at a first adjacent position, a complex between the anchoring oligonucleotide, the signaling oligonucleotide and the macromolecular entity (which can be the target) is formed. It will be recognized that the optimal density of the anchoring oligonucleotides can be tailored to the size of the target that is being detected, the size of the macromolecular entity and/or the size of the moiety for binding the macromolecular entity on the signaling oligonucleotide. The optimal density of the anchoring oligonucleotide, for example, should provide just enough space to allow for most or all of the anchoring oligonucleotides to hybridize to the signaling oligonucleotides. The anchoring oligonucleotide density used in some embodiments can be, for example, higher than $10^{11}$ molecules/cm$^2$ (or display a mean spacing lower than 10 nm). In still another embodiment, the anchoring oligonucleotide density at the surface of the substrate is equal to or higher than $10^{12}$ molecules/cm$^2$ (such as $1.4 \times 10^{12}$ molecules/cm$^2$ for generating a mean spacing of 5 nm). This optimal density may be reduced if the macromolecule-binding moiety used becomes larger (for example up to 5 kDa). In order for the assay to provide satisfactory results, the mean average between the anchoring oligonucleotide must remain lower than the average molecular size of the macromolecule (in the case of an antibody present in whole blood: lower than 12 nm). In another embodiment, when the target is a small molecule, the density of the anchoring oligonucleotides on the surface of the substrate can be made even higher (spacing lower than 5 nm) as long as the signaling oligonucleotide can still hybridize on most of the anchoring oligonucleotides.

The substrate described herein can be an "array", a term which include any one-dimensional, two-dimensional or substantially two-dimensional (as well as a three-dimensional) arrangement of addressable regions bearing an anchoring oligonucleotide associated with that region. In some embodiments, the array can be tri-dimensional, such as for example a nanoparticle, such as a gold nanoparticle or a fluorescent nanoparticle. The substrate can be substantially planar or can take a spheric form. An "addressable array" includes any one or two dimensional arrangement of discrete regions bearing particular anchoring oligonucleotides associated with that region and positioned at particular predetermined locations on the substrate (each such location being at a known "address"). These regions may or may not be separated by intervening spaces. Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand, more than ten thousand features, or even more than one hundred thousand features, in an area of less than 20 cm$^2$, such as less than 10 cm$^2$. For example, features may have widths (that is, diameter, for a round spot) in the range from a 10 µm to 1.0 cm. In other embodiments each feature may have a width in the range of 1.0 µm to 1.0 mm, such as 5.0 µm to 500 µm, including 10 µm to 200 µm. Non-round features may have area ranges equivalent to that of circular features with the foregoing width (diameter) ranges.

The third component of the system is the signaling oligonucleotide. In the detection system described herewith, the signaling oligonucleotide has a dual role of being capable of specifically binding to the target or the macromolecular entity and of modulating a signal when its reporter moiety is located in the vicinity of the surface of the substrate.

In an embodiment, the signaling oligonucleotide is a single linear oligonucleotide comprising both the target-binding moiety and the reporter moiety (that can be covalently attached to one another). In such embodiment, the signaling oligonucleotide comprises three subcomponents, a core oligonucleotide (comprising a complementary region for hybridizing with the anchoring oligonucleotide), a moiety for binding a macromolecular entity and a reporter moiety. The specific binding to the target/macromolecular entity described above is achieved by associating (preferably in a covalent manner) a moiety for binding a macromolecular entity at one end of the signaling oligonucleotide. The ability to modulate a signal described above is obtained by associating (preferably in a covalent manner) a reporter moiety at the other end of the signaling oligonucleotide. The signaling oligonucleotide is preferably a single-stranded and linear oligonucleotide. Still in the context of the detection system described herein, the signaling oligonucleotide has the ability to diffuse in solution, it is not necessarily associated to the surface of the substrate but can nevertheless hybridizes with an anchoring oligonucleotide.

In another embodiment, the signaling oligonucleotide is modular and comprises a combination at least two distinct elements: a first signaling oligonucleotide element (comprising a moiety for binding a macromolecular entity) and a second signaling oligonucleotide element (comprising the core region (as described above and comprising a complementary region for hybridizing with the anchoring oligonucleotide) and the reporter moiety). This embodiment conveniently allows the design of various signaling oligonucleotides without the need for associating a reporter moiety and a moiety for binding to a macromolecular entity to a single oligonucleotide.

Figure 3B:
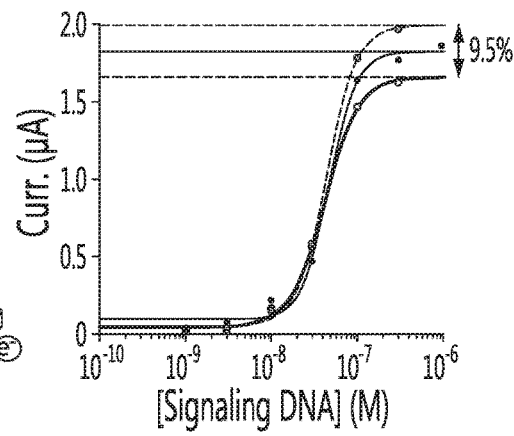
Figure 4:
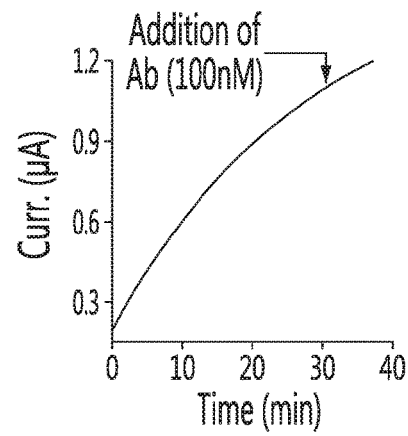
FIG. 4 illustrates that, there is no current reduction when the macromolecular target (proteins in this embodiment) binds the signaling oligonucleotides after the later are bound on the electrode surface. This was demonstrated using the Dig-antibody system (illustrated in FIG. 2) by adding the Dig-antibody (arrow in this figure) only after the anchoring oligonucleotides have been fully saturated by the signaling oligonucleotides. No signal reduction is observed following the addition of 100 nM antibodies even though we expect these antibodies to bind the ligand on the electrode-bound signaling oligonucleotide. Results are shown as the current (μA) in function of time (min). This result demonstrates that eSHHA's signaling mechanism is not linked to a binding-induced reduction of the electron rate transfer of an individual methylene blue. This result also supports a mechanism, which suggests that electrochemical signal reduction is rather linked to the fact that less signaling oligonucleotide bind to the electrode surface when these they are bound to a macromolecule or a macromolecular target.
Figure 10A:
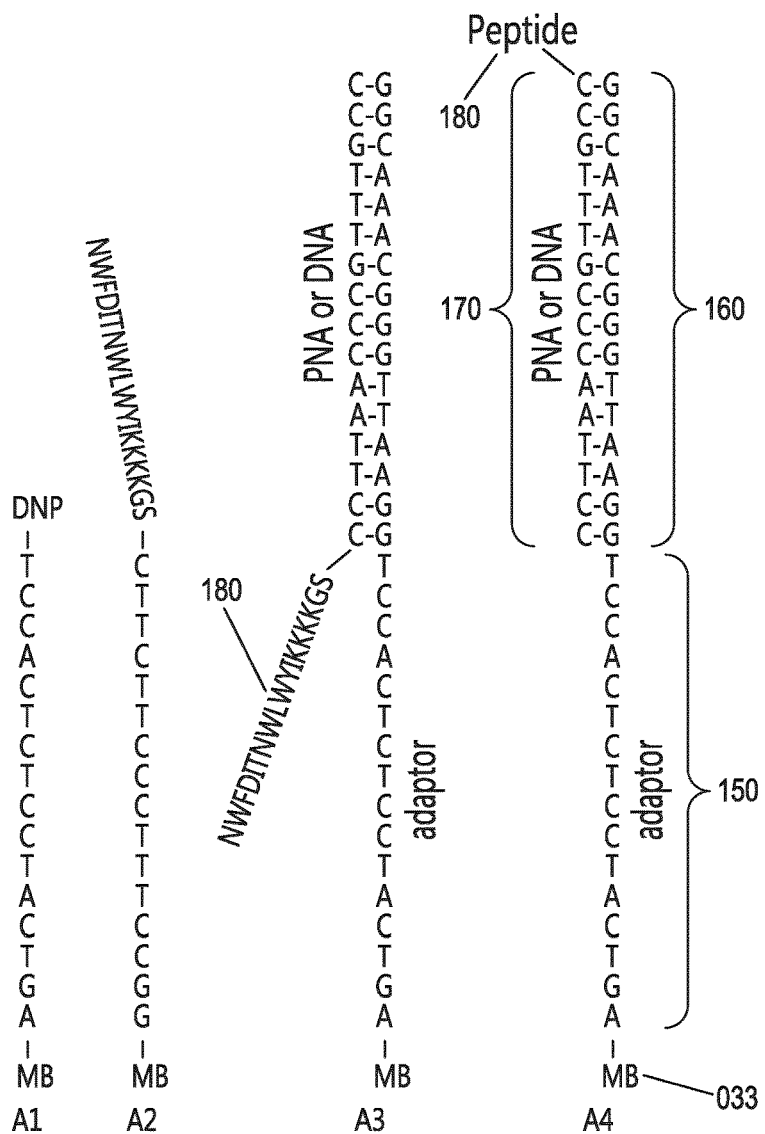
FIG. 10 illustrates an embodiment in which the signaling oligonucleotide is modular and comprises two elements. In the embodiment shown on this figure, a peptide epitope from the GP41 protein of HIV (recognized by an anti-HIV antibodies and referred to as 4E10) can be easily attached to an adaptor element when covalently linked to a labeling element. (A) For example, modular signaling oligonucleotides (A3 and A4) can be composed from two oligonucleotides: a an "adaptor" oligonucleotide (DNA) that contains a methylene blue at its 5' end and a "labeling" oligonucleotide (PNA or DNA) containing the moiety for binding a macromolecular entity (hapten or epitope) and capable of hybridizing to the adaptor oligonucleotide. In this embodiment, four signaling oligonucleotides are illustrated: (A1) a negative control unimolecular signaling oligonucleotide having a "DNP" moiety for binding a macromolecular entity, (A2) a positive control unimolecular signaling oligonucleotide having the GP41 peptide for binding a macromolecular entity, (A3-A4) modular signaling oligonucleotides having an adaptor element and a labeling element, the latter being associated with the peptide for binding a macromolecular entity. The GP41 peptide can be located towards (A3) or in opposite direction of (A4) the reporter moiety of the adaptor element. (B) Due to its larger size and its higher negative charge density the modular signaling oligonucleotides A3 ($3^{rd}$ and $4^{th}$ columns) hybridize less efficiently on the electrode surface compared to the original signaling oligonucleotide A1 ($1^{st}$ and $2^{nd}$ columns). However, the addition of 20 mM of $Mg^{2+}$ ($2^{nd}$ and $4^{th}$ columns) enables to reduce charge repulsion between the signaling oligonucleotide and allows to increase the hybridization efficiency of the modular signaling oligonucleotide (A3) at the surface of the electrode. Results are shown as current (μA) in function of signaling oligonucleotide used and the presence or absence of magnesium. These experiments were performed at room temperature in 50 mM $NaH_2PO_4$, 150 mM NaCl, pH 7.0. (C) Measure of the current (in μA) in function of time (min) for assays conducted in the presence or absence of the 4E10 HIV antibodies using the modular signaling oligonucleotide A3 (100 nM). These results were obtained in spike bovine blood using 1000 nM of antibodies and an additional 20 mM of $MgCl_2$.

An embodiment of such modular signaling oligonucleotide is shown on FIG. 10A3 and A4. As indicated above, the modular signaling oligonucleotide comprises a first oligonucleotide (adaptor element) comprising a first complementary region 150 for hybridizing with an anchoring oligonucleotide and a second complementary region 160 for hybridizing with the second element of the modular signaling oligonucleotide. In the embodiment shown on FIG. 10, the adaptor element is made of DNA. The adaptor element is, at one or near one of its ends, associated with a reporter moiety 033 (MB or methylene blue in this embodiment). The adaptor element is configured such that, upon the hybridizing with the anchoring oligonucleotide, its reporter moiety is located in the vicinity of the surface of the substrate (near the first end of the anchoring oligonucleotide). The modular signaling oligonucleotide also comprises a labeling element 170. In the embodiment shown on FIG. 10, the labeling element is made of PNA. The signaling element 170 also possesses a third complementary region for hybridizing with the first adaptor element of the modular signaling oligonucleotide. The signaling element also includes a moiety for binding a macromolecular entity (e.g., the 4E10 peptide in this embodiment). The moiety for binding a macromolecular entity can either be located internally (near the junction between the core region 150 and complementary region 160 of the first adaptor element, as shown in FIG. 10A3) or externally (near the free terminus of the first element, as shown in FIG. 10A4). In an embodiment, the moiety for binding a macromolecular entity is internally located.

The adaptor element of the modular signaling oligonucleotide can have a total length of at least 20, 21, 22, 23, 24, 25, 26, 27, 28, 29, 30, 31, 32, 33, 34, 35, 36, 37, 38, 39, 40 nucleic acid bases and/or a total length of no more than 40, 39, 38, 37, 36, 35, 34, 33, 32, 31, 30, 29, 28, 27, 26, 25, 24, 23, 22, 21 or 20 nucleic acid bases. The adaptor element also comprises a region designed for hybridizing to the anchoring oligonucleotide (referred to a first complementary region). The first complementary region is at least 10, 11, 12, 13, 14, 15, 16, 17, 18, 19 or 20 and/or no more than 20, 19, 18, 17, 16, 15, 14, 13, 12, 11 or 10 contiguous nucleic acid bases long. The level of identity between the first complementary region of the adaptor element and the corresponding complementary region of the anchoring oligonucleotide is at least 80%, 85%, 90%, 91%, 92%, 93%, 94%, 95%, 96%, 97%, 98%, 99% or 100%. In one embodiment, the entire length of the first complementary region hybridizes with a corresponding complementary region of the anchoring oligonucleotide. The adaptor element also comprises a region designed for hybridizing to the labeling element (referred to a second complementary region). The second complementary region is at least 10, 11, 12, 13, 14, 15, 16, 17, 18, 19 or 20 and/or no more than 20, 19, 18, 17, 16, 15, 14, 13, 12, 11 or 10 contiguous nucleic acid bases long. The level of identity between the second complementary region of the adaptor element and the corresponding complementary region of the labeling element is at least 80%, 85%, 90%, 91%, 92%, 93%, 94%, 95%, 96%, 97%, 98%, 99% or 100%. In one embodiment, the entire length of the second complementary region hybridizes with a corresponding complementary region of the labeling oligonucleotide. In another embodiment, the adaptor element oligonucleotide comprises additional nucleic acid bases which are not involved into the hybridizing with the anchoring oligonucleotide or the second labeling element (located 3' and/or 5' with respect to the first complementary region).

The labeling element of the modular signaling oligonucleotide can have a total length of at least 8, 9, 10, 11, 12, 13, 14, 15, 16, 17, 18, 19, 20, 21, 22, 23, 24, 25, 26, 27, 28, 29 or 30 nucleic acid bases and/or a total length of no more than 30, 29, 28, 27, 26, 25, 24, 23, 22, 21, 20, 19, 18, 17, 16, 15, 14, 13, 12, 11, 10, 9 or 8 nucleic acid bases. The labeling element also comprises a region designed for hybridizing to the adaptor element oligonucleotide (referred to a third complementary region). The third complementary region is at least 10, 11, 12, 13, 14, 15, 16, 17, 18, 19 or 20 and/or no more than 20, 19, 18, 17, 16, 15, 14, 13, 12, 11 or 10 contiguous nucleic acid bases long. The level of identity between the third complementary region and the second complementary region of the adaptor element is at least 80%, 85%, 90%, 91%, 92%, 93%, 94%, 95%, 96%, 97%, 98%, 99% or 100%. In one embodiment, the entire length of the third complementary region hybridizes with the second complementary region of the adaptor element. In another embodiment, the labeling element comprises additional nucleic acid bases which are not involved into the hybridizing with the second complementary region of the adaptor element (located 3' and/or 5' with respect to the third complementary region).

The core and complementary regions of the oligonucleotides described herein is composed of any combination of known natural or synthetic nucleic acid bases and its backbone can be modified from naturally-occurring backbones. Naturally-occurring oligonucleotides contain phosphodiester bonds and synthetic oligonucleotides comprising nucleic acid analogs may have alternate backbones, comprising, for example, phosphoramide, phosphorothioate, phosphorodithioate, O-methylphosphoroamidite linkages and peptide nucleic acid backbones and linkages. Other analog nucleic acids analogs include those with positive backbones, non-ionic backbones, and non-ribose backbones. Nucleic acids bases containing one or more carbocyclic sugars are also included within the definition of contemplated nucleic acid bases.

The core and complementary regions of the signaling oligonucleotides generally have a total length between 10 and 40 nucleic acid bases. The length and composition (GC and AT content) of the core region of the signaling oligonucleotide is designed in order to achieve a sufficiently good affinity between the anchoring and signaling oligonucleotides or between the first and the second signaling oligonucleotide (for example, a $K_D$ of at least 10 nM). When the signaling oligonucleotide is unimolecular, the core/complementary regions of the signaling oligonucleotide can have a total length of at least 10, 11, 12, 13, 14, 15, 16, 17, 18, 19, 20, 21, 22, 23, 24, 25, 26, 27, 28, 29 or 30 nucleic acid bases and/or a total length of no more than 30, 29, 28, 27, 26, 25, 24, 23, 22, 21, 20, 19, 18, 17, 16, 15, 14, 13, 12, 11 or 10 nucleic acid bases. The core oligonucleotide region of the signaling oligonucleotide also comprises a sub-region designed for hybridizing to the anchoring oligonucleotide or the first signaling oligonucleotide (referred to a complementary region). The complementary region of the signaling oligonucleotide is at least 10, 11, 12, 13, 14, 15, 16 or 17 and/or no more than 17, 16, 15, 14, 13, 12, 11 or 10 contiguous nucleic acid bases long. The level of identity between the complementary regions of the signaling oligonucleotide and the anchoring oligonucleotide is at least 80%, 85%, 90%, 91%, 92%, 93%, 94%, 95%, 96%, 97%, 98%, 99% or 100%. In one embodiment, the entire length of the core oligonucleotide region of the signaling oligonucleotide is complementary to the a corresponding complementary region of the anchoring oligonucleotide. In another embodiment, the core region of the signaling oligonucleotide comprises additional nucleic acid bases which are not involved into the hybridizing with the anchoring oligonucleotide (located 3' and/or 5' with respect to the complementary region).

The moiety for binding the macromolecular entity associated at one end of the signaling oligonucleotide can be any entity which is capable of binding to the target itself or a macromolecular entity. In an embodiment, each signaling oligonucleotide has at most one (e.g., a single) target moiety region. The moieties for binding a macromolecular entity include, but are not limited to, proteins, peptides (including antigens and epitopes), carbohydrates, nucleic acids, lipids, small molecules, and the like. In an embodiment in which the target is an antibody or a lectin, the moiety can be or comprise an epitope specific to such antibody or lectin. The moiety can also be an aptamer (e.g., a nucleic acid-based sequence capable of binding to a polypeptide), a further oligonucleotide moiety (e.g., when the target is a complementary nucleic acid-based molecule), a lipid (e.g., when the target is a lipid-binding entity), etc. In an embodiment, the moiety can be a nucleic acid moiety having between 8 to 20 nucleic acid residues. In another embodiment, the moiety be a glycosylated or non-glycosylated peptide having between 2 to 60 amino acid residues. In still another embodiment, the moiety can be a polysaccharide having between 2 to 30 carbohydrate units.

It is contemplated that the signaling oligonucleotide be associated with the moiety for binding the macromolecular entity either via a terminal nucleic acid base (e.g., its 5' or 3' nucleic acid terminus) or via an internal nucleic acid base, preferably located within the five nucleic acid bases adjacent to the 5' or 3' nucleic acid terminus of the signaling oligonucleotide. In an embodiment, the signaling oligonucleotide is attached via its first end in a covalent manner to the moiety for binding the macromolecular entity. The signaling oligonucleotide can be associated directly to the moiety or, alternatively, can be associated to the moiety through the use of a linker. In embodiments of the system in which the signaling oligonucleotide is associated to target-binding moiety indirectly via a linker, it is contemplated that the linker can be any linker which will allow the creation of steric hindrance at the surface of the substrate when the signaling oligonucleotide binds to the target and the anchoring oligonucleotide. In an embodiment, the linker moiety may include 1 to 25 carbon atoms, such as 2 to 20 carbon atoms, including 5 to 15 carbon atoms. In an embodiment, the linker is a alkyl, such as a straight chain lower alkyl (e.g., $C_1$ to $C_{10}$ lower alkyl), and preferably a $C_3$ to $C_6$ alkyl. In some embodiments, the linker is a $C_6$ straight-chain alkyl.

The reporter moiety region associated to the other end (e.g., also referred to the "second end", the end of the signaling oligonucleotide not associated with the moiety for binding the macromolecular entity) of the signaling oligonucleotide can be any entity which is modulating a signal when it is in close association with the surface of the substrate. It is important that the signaling oligonucleotide be configured such that, upon hybridizing with the anchoring oligonucleotide, the reporter moiety be located closer to the surface of the substrate than the moiety for binding the macromolecular entity. For example, if the anchoring nucleotide is associated via its 3' terminus to the surface of the substrate, then the reporter moiety must be located at the 5' end of the signaling oligonucleotide (and vice versa). Reporter moieties include, but are not limited to, fluorophore, quenchers, enzymes, enzyme activators, enzyme inhibitors, redox-reporter, etc.

It is contemplated that the signaling oligonucleotide be associated with the reporter moiety either via a terminal nucleic acid base (e.g., its 5' or 3' nucleic acid terminus) or via an internal nucleic acid base, preferably located within the five nucleic acid bases adjacent to the 5' or 3' nucleic acid terminus of the signaling oligonucleotide. In an embodiment, the signaling oligonucleotide is attached via its second end in a covalent manner to the reporter moiety. The signaling oligonucleotide can be associated directly to reporter moiety or, alternatively, can be associated to the reporter moiety through the use of a linker. In embodiments of the system in which the signaling oligonucleotide is associated to reporter moiety indirectly via a linker, it is contemplated that the linker can be any linker which will allow the location of the reporter moiety in the vicinity of the surface of the substrate when the anchoring and the signaling oligonucleotides are hybridized. In an embodiment, the linker moiety may include 1 to 25 carbon atoms, such as 2 to 20 carbon atoms, including 5 to 15 carbon atoms. In an embodiment, the linker is a alkyl, such as a straight chain lower alkyl (e.g., $C_1$ to $C_{10}$ lower alkyl), and preferably a $C_3$ to $C_6$ alkyl. In some embodiments, the linker is a $C_6$ straight-chain alkyl.

The substrate may be a fluorescent substrate (e.g., comprising a fluorophore or a plurality of fluorophores) and the reporter moiety can be a corresponding quencher moiety (or a combination of quencher moieties). Alternatively, the reporter moiety can be a fluorophore (or a combination of fluorophores) and the substrate may be a corresponding quencher (e.g., comprising a quencher or a plurality of quenchers). In these instances, in the absence of target most of the signaling oligonucleotides will hybridize with the anchoring oligonucleotide, the distance the fluorophore is held from the quencher is sufficient to minimize, suppress, or prevent the fluorophore from emitting a detectable signal. Alternatively, in the presence of the target or the macromolecular entity, less signaling oligonucleotides are able to localize at the surface of the substrate and the fluorophore can emit a detectable signal. The term "fluorophore" refers to any molecular entity that is capable of absorbing energy of a first wavelength and re-emit energy at a different second wavelength. The fluorophore may be synthetic or biological in nature, as known to those of skill in the art. More generally, any fluorophore can be used that is stable under assay conditions and that can be sufficiently suppressed when in close proximity to the quencher such that a significant change in the intensity of fluorescence of the fluorophore is detectable in response to target specifically binding the probe. Examples of suitable fluorophores include, but are not limited to CAL Fluor Red 610 (FR610; Biosearch Technologies, Novato, Calif.), fluorescein isothiocyanate, fluorescein, 6-carboxyfluorescein (6-FAM), rhodamine and rhodamine derivatives, coumarin and coumarin derivatives, cyanine and cyanine derivatives, Alexa Fluors™ (Molecular Probes, Eugene, Oreg.), DyLight Fluors (Thermo Fisher Scientific, Waltham, Mass.), and the like.

The term "quencher" may refer to a substance that absorbs excitation energy from a fluorophore and dissipates that energy as heat. The quencher may also absorb excitation energy from a fluorophore and dissipate that energy as re-emitted light at a different wavelength. Quenchers are used in conjunction with fluorophores, such that when the quencher is positioned adjacent the fluorophore or at a distance sufficiently close to the fluorophore, the emission of the fluorophore is suppressed. However, when the quencher is positioned away from the fluorophore or at a distance sufficiently far from the fluorophore, the emission of the fluorophore is not suppressed, such that a signal of the fluorophore is detectable. Alternatively, the quencher may include moieties that reduce the emission of the fluorophore via photoelectron transfer, resonance energy transfer or other quenching mechanisms. The quencher may also be replaced by a second fluorophore capable of resonance energy transfer, by a second fluorophore capable of forming an excimer or exiplex or, in general, by any other group that modulates the fluorescence of the first fluorophore. The quencher may be synthetic or biological in nature, as known to those of skill in the art. More generally, any quencher can be used that is stable under assay conditions and that can sufficiently suppress the fluorescence of the fluorophore when in close proximity to the fluorophore such that a significant change in the intensity of fluorescence of the fluorophore is detectable in response to target/macromolecular entity specifically binding the signaling oligonucleotide. Examples of quenchers include, but are not limited to, Black Hole Quencher (BHQ; Biosearch Technologies, Novato, Calif.), Dabsyl (dimethylaminoazosulphonic acid), Qxl quenchers (AnaSpec Inc., San Jose, Calif.), Iowa black FQ, Iowa black RQ, and the like. In another embodiment the quencher may also be fluorescent, leading to emission at a second wavelength when the quencher is in proximity to the first fluorophore. Examples of such fluorophore/quencher pairs include Alexa488™-Alexa555™, Alexa488™-Cy3™, Cy3™-Cy5™. In other embodiments, the quencher is a second fluorophore that forms an excimer or an exciplex with the first fluorophore, leading to a change in fluorescence upon their segregation. An example would include an embodiment in which both the fluorophore and the quencher are pyrene.

In certain embodiments, the substrate and the reporter moiety of the present disclosure include a first signaling moiety that includes a macromolecule having a catalytic activity and a second signaling moiety that includes an inhibitor or an activator of the catalytic activity. In certain embodiments, the catalytic macromolecule is held at distance in close proximity to the inhibitor, such as adjacent the inhibitor, by complementary hybridizing of the anchoring and signaling oligonucleotides.

In still another embodiment, the substrate is a metallic electrode (such as a gold, silver, platinum) or a non-metallic electrode (e.g., carbon or silicon for example). The conductive and semiconductive materials can be metallic or non-metallic.) and the reporter moiety is a redox reporter (e.g., organic redox moieties, such as viologen, anthraquinone, ethidium bromide, daunomycin, methylene blue, and their derivatives, organo-metallic redox moieties, such as ferrocene, ruthenium, bis-pyridine, tris-pyridine, bis-imidizole, and their derivatives, and biological redox moieties, such as cytochrome c, plastocyanin, and cytochrome c'). When no complex between the anchoring oligonucleotide, the signaling oligonucleotide and the macromolecular entity is formed, the signaling oligonucleotides hybridize with the anchoring oligonucleotides and the reporter moiety localizes closely to the surface of the substrate, thereby creating current. When complexes between the anchoring oligonucleotide, the signaling oligonucleotide and the macromolecular entity are formed, less of the signaling oligonucleotides are capable of hybridizing with the anchoring oligonucleotides, less reporter moieties localize to the surface of the substrate and less current is produced.

In embodiments in which multiplex detection (e.g., more than one type of targets) is warranted, the system can comprises, for each type of target being detected, a specific combination of an anchoring oligonucleotide and a corresponding signaling oligonucleotide bearing a moiety either specific for each of the targets or capable of binding a macromolecular entity which also specifically binds one of the targets. The nucleic acid sequence between the anchoring/signaling oligonucleotide of each of the combination differs so as to allow/limit specific binding between the anchoring oligonucleotide and the signaling oligonucleotide for each different targets. The anchoring oligonucleotides of each combination of this multiplex system can be associated to the surface of different substrates or at different known locations on the surface of the substrate. Further, in order to allow steric hindrance at the surface of the substrate, the density of the anchoring oligonucleotides on the substrate prevents or limits the formation of a complex between at least one anchoring oligonucleotide, at least one signaling oligonucleotide and at least one target at two adjacent locations on the substrate.

Figure 9B:
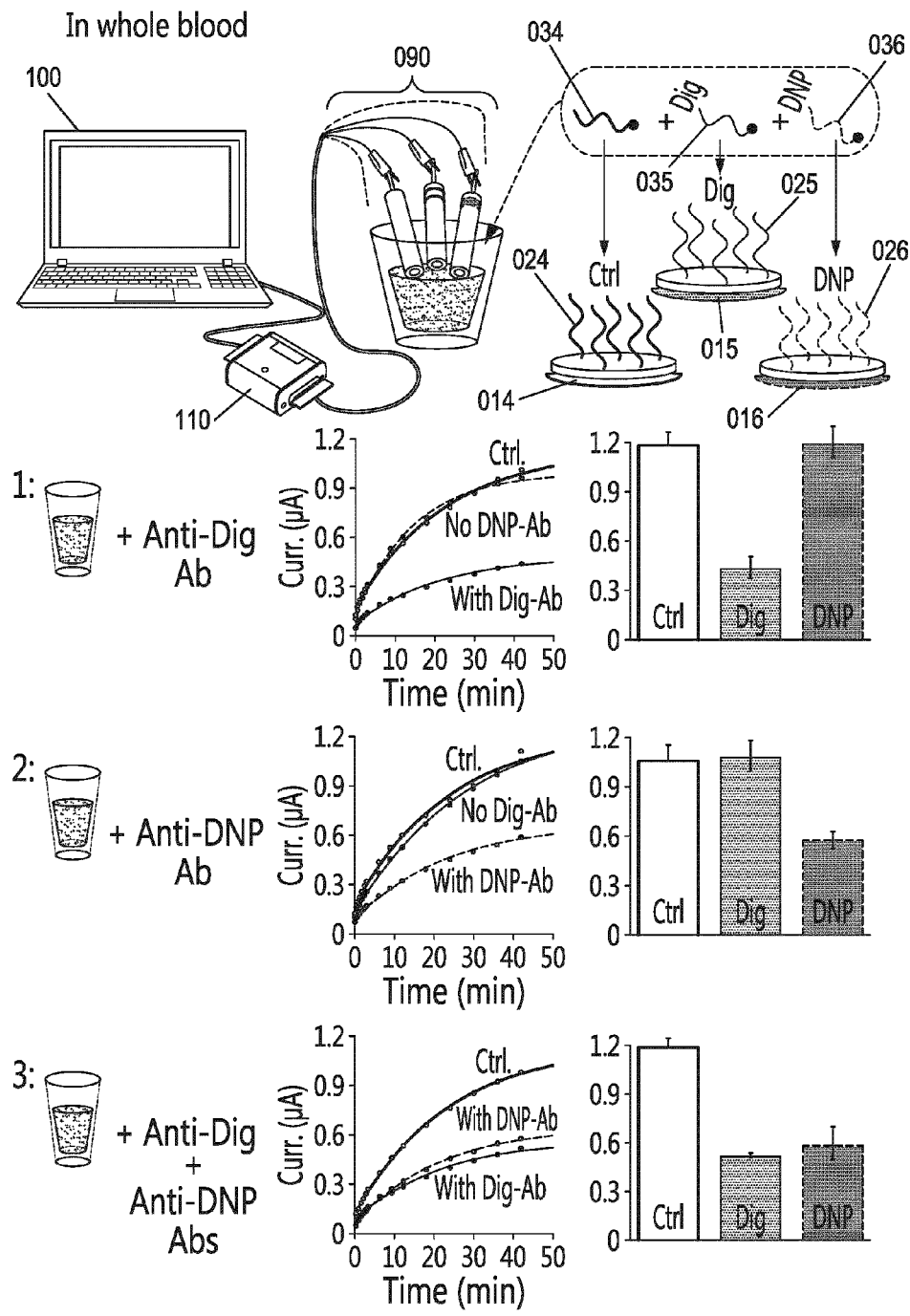
FIG. 9 illustrates that eSHHA performs equally well in whole blood and enables the simultaneous detection of multiple antibodies. (A) eSHHA performs equally well in buffer (1) and whole blood (2). Results are shown as current (μA) in function of time (min) in the presence (●) and absence (○) of the macromolecular target (antibody in this figure). (B) eSHHA performs well in a multiplexed format. Three electrodes, each functionalized with a specific anchoring oligonucleotide are used to simultaneously detect different antibodies. The control (Ctrl) electrode (014) hybridizes to a signaling oligonucleotide (034) bearing no moiety for binding the macromolecular entity. The DIG electrode (015) hybridizes to a signaling oligonucleotide (035) bearing a digoxigenin moiety for binding anti-DIG antibodies. The DNP electrode (016) hybridizes to a signaling oligonucleotide (036) bearing a DNP moiety for binding anti-DNP antibodies. The whole blood samples were first spiked with the above-mentioned antibodies (or no antibody) and 100 nM of all the three signaling oligonucleotide were added seconds before the acquisition. Current (in μA) was measured in whole blood spiked with anti-DIG antibodies (1 and 3) or anti-DNP antibodies (2 and 3). (C) Current density (in $\mu A/cm^2$) in function of voltage (in V) was measured electrodes after 5 seconds, 6 minutes, 18 minutes and 30 minutes of incubation in whole blood spiked with anti-DIG antibodies.

An embodiment of a multiplex system is illustrated in FIG. 9B. In this figure, whole blood is spiked with one or two different antibodies and three systems are used. The person skilled in the art will understand that other types of samples than blood can be submitted to this multiplex detection and that more than two different targets can be detected with multiplex detection. In the embodiment shown in FIG. 9B, a plurality of sensors 090 are provided. Each of the electrode sensor 090 comprises a different substrate (014, 015 or 016) each associated with a distinct type of anchoring oligonucleotide (023, 025 or 026 respectively). In the context of the present disclosure, the term "distinct" refers to the nucleic acid sequence of the anchoring oligonucleotides being different between each of the sensor. The anchoring oligonucleotides present on a single sensor have the same nucleic acid sequence. Otherwise stated, the anchoring oligonucleotides 024, 025 and 026 (each associated with substrate 014, 015 and 016) have a distinct nucleic acid sequence which allows them to specifically bind to signaling oligonucleotide 034, 035 and 036 (respectively). It follows that each of the signaling oligonucleotides 034, 035 and 036 also have a distinct nucleic acid sequence. Signaling oligonucleotide 034, substrate 014 and anchoring oligonucleotide 024 are part of a reference or control electrode sensor and their presence is optional in the multiplex system. Signaling oligonucleotide 034 is associated at one of its end with a reporter moiety but lacks any moiety for binding a macromolecular entity/target. Signaling oligonucleotide 035, substrate 015 and anchoring oligonucleotide 025 (collectively referred to as the "Dig electrode") are designed to detect (and optionally quantify) a first target, anti-digoxigenin antibodies in the embodiments of FIG. 9. As such, signaling oligonucleotide 035 has, at one of its end, a digoxigenin moiety attached thereto and, at the other end, a reporter moiety. Signaling oligonucleotide 036, substrate 016 and anchoring oligonucleotide 026 (collectively referred to as the "DNP electrode") are designed to detect (and optionally quantify) a second target, namely anti-DNP antibodies. As such, signaling oligonucleotide 036 has, at one of its end, a DNP attached thereto and, at the other end, a reporter moiety.

As shown in the top panel of FIG. 9B, when blood is spiked with anti-digoxigenin antibodies, a strong signal is provided from the reference electrode (control) and the DNP electrode because, on such electrodes, no complex with the anti-digoxigenin antibodies is formed at the surface of the substrate. However, a reduction in the signal from the Dig electrode is observed because complexes form between the anti-digoxigenin antibodies, the signaling oligonucleotides 035 and the anchoring oligonucleotide 025, thereby causing steric hindrance on the surface of the substrate.

As shown in the middle panel of FIG. 9B, when blood is spiked with anti-DNP antibodies, a strong signal is provided from the reference electrode (control) and the Dig electrode because, on such electrodes, no complex with the anti-DNP antibodies is formed at the surface of the substrate. However, a reduction in the signal from the DNP electrode is observed because complexes form between the anti-DNP antibodies, the signaling oligonucleotides 036 and the anchoring oligonucleotide 026, thereby causing steric hindrance on the surface of the substrate.

As shown in the lower panel, when blood is spiked with anti-digoxigenin antibodies and anti-DNP antibodies, a strong signal is provided from the reference electrode (control) because, on such electrode, no complex with the anti-digoxigenin or the anti-DNP antibodies is formed at the surface of the substrate. However, a reduction in the signal from the Dig electrode and the DNP electrode is observed because complexes form between the anti-digoxigenin antibodies, the signaling oligonucleotides 035 and the anchoring oligonucleotide 025 or between the anti-DNP antibodies, the signaling oligonucleotides 036 and the anchoring oligonucleotides 026, thereby causing steric hindrance on the surface of the substrates.

In additional embodiments, it may be convenient to be provided with a control system. This control system can also comprise anchoring oligonucleotides associated at an appropriate density (similar to the detection or multiplex system described herein) on the surface of a substrate. However, the control signaling oligonucleotides do not comprise moiety for binding a macromolecular entity or a target. The control signaling oligonucleotides do however bear, at one of their end, a reporter moiety. In such embodiment, the amount of hybridizing between the anchoring oligonucleotide and the signaling oligonucleotide will not differ in the presence or in the absence of the target because no steric hindrance caused by the target/macromolecular entity can be generated.

The present disclosure also provides kits and commercial packages comprising the detection, multiplex or control systems described herein. The kit can comprise any one of a reaction vessel (such as an electrode) for each substrate that is being provided, a control sample known of lacking the target(s) intended to be detected, a control sample containing a known amount of the target(s) intended to be detected, a control value or a set of control values associated with the lack or the presence of known amounts of the target(s), solution or suspension comprising the substrate or the signaling oligonucleotides as well as instructions on how to determine the presence/quantity of the target(s) based on the system that is provided. The instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-ray®, computer-readable memory, etc., on which the information has been recorded or stored. Yet another means that may be present is a website address which may be used via the Internet to access the information at a removed site.

Methods and Associated Applications

The present disclosure also provides a method for the detection of a target or a plurality of target in a sample. The methods described herein can be configured for a "signal-on" or a "signal-off" detection of the target or the plurality of targets. The methods can also be configures for quantifying the amount of the target or the plurality of targets.

The methods described herein first comprise providing a sample suspected of having the target or the plurality of targets. Embodiments of the sample have been described above and do apply herein. In some embodiment, the sample is used without being submitted to a prior fractionation or an amplification. In other embodiments, the sample can be fractionated, diluted or amplified to enrich the sample for the target or the plurality of targets intended to be detected.

Once the sample (or a diluted or enriched fraction thereof) has been obtained, it is contacted with the detection system (monoplex or multiplex) described herein under conditions so as to allow the formation of the complex between the at least one anchoring oligonucleotide, the at least one signaling oligonucleotide and the macromolecular entity. The methods disclosed herein may be carried out in any reaction medium that allows specific binding between the anchoring, the signaling oligonucleotides and the macromolecular entity as defined herein. In cases where the sample contains a macromolecule target that specifically binds to the target binding moiety of the signaling oligonucleotides, specific hybridizing between the anchoring oligonucleotide and the signaling oligonucleotide may be limited or prevented due to the steric hindrance caused by the macromolecule target. In cases where the sample contains a target and that the system comprises a further macromolecular entity that specifically binds to the moiety of the signaling oligonucleotides, specific hybridizing between the anchoring oligonucleotide and the signaling oligonucleotide is not limited or prevented due to the steric hindrance caused by the macromolecular entity (which preferably interacts with its cognate target).

Once the sample has been contacted with the system (or the plurality of systems), the method comprises determining the amount of anchoring oligonucleotides having hybridized with signaling oligonucleotides to obtain a test value or test amount. The presence/absence of binding of a target/macromolecular entity to the signaling oligonucleotides will modulate the amount of hybridized anchoring/signaling oligonucleotides and ultimately modulate the amount of reporter moiety located in the vicinity of the surface of the substrate. Such modulation is indicative of the amount of hybridized anchoring/signaling oligonucleotides and ultimately of the amount targets in the sample. As such, the method comprises a step of determining the amount (directly or indirectly) of the plurality of anchoring oligonucleotides having hybridized with the plurality of signaling oligonucleotides.

In order to make a proper detection of the target, an amount of anchoring oligonucleotides having hybridized with the signaling oligonucleotides in the absence of the target can be provided (as a pre-determined value) or determined (see below how to determine the control value).

Once the amount of the anchoring oligonucleotides having hybridized with the signaling oligonucleotides in the presence of the sample has been determined, the sample can then be characterized. This characterization is possible because a comparison between the test amount of the anchoring oligonucleotides having hybridized with the signaling oligonucleotides in the presence of the sample and the control amount is being made. If it is determined that the test amount is lower than the negative control amount, then the sample is characterized has having the target. An optional step of quantification of the target can be performed if the test amount is lower than the negative control amount. If it is determined that the test amount is the same or higher than the negative control amount, then the sample is characterized has lacking the target.

In another embodiment, when a positive control amount is used, the characterization step could include comparing the test amount with a plurality of positive control amounts and determining which of the positive control amounts is closest to the test amount to detect, and optionally quantify the target.

In order to confirm the presence of the target or quantity the amount of the target, the method also comprises providing a control amount for comparison with the test amount. In an embodiment, the control value can be obtained by contacting a control sample (e.g., a sample known to lack the target) with the detection system (monoplex or mulitplex) described herein and determining the amount of anchoring oligonucleotides having hybridized with signaling oligonucleotides. In this embodiment, a control or background signal will be obtained and can be used as a control amount. In another embodiment, the control amount can be obtained by contacting the same sample that is being detected with a control system. As indicated above, such control system lack any moiety for binding the macromolecular entity or the combination of macromolecular entities which are being detected. In yet another embodiment, the control value can be provided from a detection system comprising a known amount of the target (e.g., positive controls). Numerous alternative controls may be performed individually or in combination, as is known to those of skill in the art.

The method described herein also comprise comparing the test amount obtained with the control value obtained to determine the presence, and optionally the quantity, of the target in the sample. This comparison can be made by a person or by a computer-implemented method using, for example, the apparent dissociation constant ($K_D$) determined by a calibration curve.

Binding reactions involving the oligonucleotides disclosed herein may be carried out in the presence of agents and additives that promote the desired specific binding, diminish nonspecific background interactions, inhibit the growth of microorganisms, or increase the stability of the probe and/or target. Binding reactions of the disclosure may be carried out at ambient temperature, although any temperature in the range allowing specific binding may be used. For instance in some embodiments, the temperature range is from 5° C. to 45° C., such as from 10° C. to 40° C., or from 20° C. to 30° C. In addition, in some embodiments, when the target is from a biological system, the pH of the binding reaction medium is about physiological pH. For example, the pH may range from 4 to 10, such as 5 to 9, including 6 to 8. In certain cases, the pH may be 7. For convenience, reaction conditions may be chosen to allow specific binding to occur as rapidly as possible. Binding times as short as seconds (e.g., 1 to 60 seconds), or minutes (e.g. 1 to 30 minutes) may be employed. By way of example, times of 1 to 60 seconds, such as 10 to 60 seconds, including 20 to 60 seconds may be used. In other embodiments, times of 1 to 30 minutes, such as 5 to 20 minutes, including 10 to 20 minutes may be used. In some specific embodiments, especially when a nucleic acid molecule (such as DNA) is used as a moiety for binding macromolecular entities, a buffer containing cations (for example divalent cations such as magnesium cations) can be used to limit/prevent charge repulsion.

As indicated above, the density of the anchoring oligonucleotide on the surface of the substrate is important to generate steric hindrance by the complex form. As such, the method can optionally comprise a control step of determining if steric hindrance is indeed generated in the presence of the complex. Further, the method can optionally initially comprise a step of determining the density of the anchoring oligonucleotide based on the molecular weight of each of the target/macromolecular entity.

When whole blood or other complex mixture is used as a sample, it is advantageous to use a method relying on the generation of an electrochemical to provide a test value and a control value. In such embodiment, the substrate can be configured to be an electrode and the reporter moiety on the signaling oligonucleotide can be a redox reporter moiety. When the anchoring oligonucleotides and the signaling oligonucleotides are hybridized (and in part because the reporter moiety is located to end of the anchoring oligonucleotide which is associated with the surface of the substrate), the distance between the electrochemical reporter is held from the electrode is sufficient to produce a detectable signal. However, when the signaling oligonucleotides are freely diffusing in the sample or incapable of hybridizing with the anchoring oligonucleotide (due to steric hindrance from an adjacent complex), the electrochemical reporter is able to move to a distance further away from the electrode and produce a detectable decrease in the signal.

The methods described herein find use in a variety of different applications where determination of the presence or absence, and/or quantification of one or more targets in a sample is desired.

For example, the presence or absence or persistence of a target in a sample or significant changes in the concentration of a target over time can be used to diagnose/assess disease risk, presence of disease in an individual, or to tailor treatments for the disease in an individual. For example, the presence of a particular target or panel of targets may influence the choices of drug treatment or administration regimes given to an individual. In evaluating potential drug therapies, the presence, absence, or concentration of a target may be used as a surrogate for a natural endpoint such as survival or irreversible morbidity. If a treatment alters the target, which has a direct connection to improved health, the target can serve as a surrogate endpoint for evaluating the clinical benefit of a particular treatment or administration regime. Thus, personalized diagnosis and treatment based on the particular target or panel of targets detected in an individual are facilitated by the subject systems and methods. Furthermore, the early detection of targets associated with diseases is facilitated by the high sensitivity of the subject systems and methods, as described above. Due to the multiplex capability of detecting multiple targets in a single assay, combined with selectivity, sensitivity and ease of use, the presently disclosed systems and methods find use in quantitative, point-of-care or near-patient bio-molecular assays.

In a further example, the presence or absence of an infectious agent (such as a bacteria which can, in some embodiments, be resistant to one or more antibiotic) can be detected in biological samples, food or water.

In still another example, the presence or absence or persistence of a target in a sample or significant changes in the concentration of a target over time can be used to determine the contamination risk, presence of contamination in food.

The subject systems and methods find use in diagnostic assays, such as, but not limited to, the following: detecting and/or quantifying targets, as described above; screening assays, where samples are tested at regular intervals for asymptomatic subjects; prognostic assays, where the presence and or quantity of a target is used to predict a likely disease course; stratification assays, where a subject's response to different drug treatments can be predicted; efficacy assays, where the efficacy of a drug treatment is monitored; and the like.

The subject systems and methods also find use in validation assays. For example, validation assays may be used to validate or confirm that a potential disease biomarker is a reliable indicator of the presence or absence of a disease across a variety of individuals. The short assay times for the subject systems and methods may facilitate an increase in the throughput for screening a plurality of samples in a minimum amount of time.

In certain embodiments, the subject systems and methods find use in detecting antibodies in a sample. In some cases, the subject systems and methods may be used to detect the presence or absence of particular antibodies, as well as an increase or decrease in the concentration of particular antibodies in a sample.

In another embodiment, the subject systems can be used to screen for agents capable of modulating the binding between two biological entities. For example, the systems can be used to screen drug libraries and identify antagonist or agonists capable of increasing or lowering the binding between two biological entities where at least one of the biological entities (or a fragment therefrom) is associated with the signaling oligonucleotide. If the agent is capable of disrupting the interaction between the two biological entities, more signaling oligonucleotides will hybridize to the substrate's surface via the anchoring oligonucleotides If the agent is capable of facilitating the interaction between the two biological entities, less signaling oligonucleotides will hybridize to the substrate's surface via the anchoring oligonucleotides. In such embodiment, the sample that can be screened can be, for example, a cellular extract, nuclear extract, whole blood, a substantially pure form of the agent, etc.

The present invention will be more readily understood by referring to the following examples which are given to illustrate the invention rather than to limit its scope.

EXAMPLE

In response to limitations of existing technology (signal drift in whole blood, weak electrochemical current), a versatile signal transduction mechanism called "Steric-Hindrance Hybridization Assay" (SHHA) is herewith presented. SHHA relies on a novel mechanism, which exploits steric hindrance effect at the nanoscale. More specifically, it takes advantage of both the high specificity and selectivity of DNA hybridization and the difference in size between macromolecules such as proteins (>5 nm) compared to the relatively small diameter of DNA helix (<2 nm) (FIG. 1A).

In an electrochemical format, this assay consists of a free signaling DNA oligonucleotide, bearing at its extremities a specific recognition element and a signaling electro-active moiety (here, methylene blue) that can hybridize to a complementary anchoring DNA oligonucleotide previously attached to the surface of a gold electrode at high surface density. Upon binding to the anchoring oligonucleotides, the signaling oligonucleotides generate a large electrochemical signal by bringing the methylene blue (MB) redox label close to the electrode surface (FIG. 1B, solid curve). In the presence of a large macromolecule that binds to the recognition element on the signaling oligonucleotide, fewer copies of this oligonucleotide are able to reach and hybridize to the surface bound anchoring oligonucleotide due to nanoscale steric-hindrance therefore generating lower electrochemical currents (FIG. 1B, dashed curve).

eSHHA offers two main advantages over other one-step DNA-based electrochemical assays for protein detection. First, its signaling moiety is not bound to the electrode surface, which should ensure that the sensor remains largely insensitive to non-specific adsorption of potential interfering components (e.g. blood proteins) taking place in the first minutes following sensor immersion in blood. Second, the high density of anchoring oligonucleotides at the surface of the electrode will contribute to bring order of magnitude more signaling oligonucleotides to the surface thus ensuring electrochemical currents that are order of magnitude higher than the above mentioned assays.

Reagents. Tris(2-carboxyethyl) phosphine hydrochloride (TCEP; Invitrogen, Eugene, Oreg.), 6-Mercapto-1-hexanol (MCH; Fluke) and sulfuric acid (Fisher Scientific), were all used as received. Polyclonal anti-Dig (Roche Diagnostics, Indianapolis, Ind.) and streptavidin (Sigma Aldrich) were dissolved in 50 mM $NaH_2PO_4$, 150 mM NaCl, pH 7.0. Anti-DNP (whole antiserum) (Sigma Aldrich) and the other protein stocks were aliquoted and stored at 4° C. for immediate use or at −20° C. for long term storage. Newborn calf whole blood was aliquoted and frozen at −20° C. prior to use.

DNA Sequences. DNA oligonucleotides used in this manuscript were HPLC purified and synthesized by Biosearch Technologies Inc., Novato, Calif. The thiolated anchoring oligonucleotides were used as received without further purification. Digoxigenin/methylene blue-, Biotin/methylene blue-, and DNP/methylene blue-tagged signaling oligonucleotides were used as received. The sequences of the various oligonucleotides used in this work are shown in Table 1.

TABLE 1

Sequences of different DNA oligonucleotides:
Signaling and anchoring DNA oligonucleotides

| Anchoring oligonucleotides | |
|---|---|
| Dig/biotin | 5'-HS-$(CH_2)_6$- AAGG AAA GGG AAG AAG (SEQ ID NO: 1) |
| Ctrl. | 5'-HS-$(CH_2)_6$- GAGA GGG AAA AAG GAG (SEQ ID NO: 2) |
| DNP | 5'-HS-$(CH_2)_6$- TCAG TAG GAG AGT GGA (SEQ ID NO: 3) |
| Signaling oligonucleotides | |
| Dig | 5'-Digoxigenin-CTT CTT CCC TTT CCTT-MB (SEQ ID NO: 4) |
| Biotin | 5'-Biotin-CTT CTT CCC TTT CCTT-MB (SEQ ID NO: 4) |

TABLE 1-continued

Sequences of different DNA oligonucleotides:
Signaling and anchoring DNA oligonucleotides

| | |
|---|---|
| DNP | 5'-DNP-TCC ACT CTC CTA CTGA-MB (SEQ ID NO: 5) |
| Ctrl. | 5'- CTC CTT TTT CCC TCTC-MB (SEQ ID NO: 6) |

Electrode cleaning and sensor preparation. Briefly, polycrystalline gold disk electrodes (2 mm diameter; BAS, West Lafayette, Ind.) were prepared by polishing their surfaces with diamond and alumina (BAS, West Lafayette, Ind.), with sonication in ethanol or water after each step. Following polishing, we performed electrochemical cleaning (a series of oxidation and reduction cycling in 0.5M $H_2SO_4$, 0.01M KCl/0.1M $H_2SO_4$, and 0.05M $H_2SO_4$) and area determination (based on the area of the gold oxide reduction peak in the final cleaning step) (Xiao et al., 2007).

Anchoring DNA oligonucleotides (0.1 mM) were incubated with TCEP (1 µM) for 1 hr to allow reduction of disulfide bonds. This solution was diluted to 100 nM (or other concentrations when generating electrodes at lower DNA packing density) in 50 mM sodium phosphate, 150 mM NaCl, pH 0.7.0. Electrodes (thoroughly rinsed with DI water) were incubated in 150 µL of 100 nM solution of anchoring oligonucleotides for 2 hr. Electrodes were then rinsed with DI water, and incubated in 3 mM MCH in buffer for another 3 hr to displace nonspecifically adsorbed DNA and passivate the remaining electrode area. After thoroughly rinsing with DI water, electrodes were stored in buffer. The anchoring oligonucleotide surface density (i.e., the number of electroactive DNA moles per unit area of the electrode surface) determined for these conditions by using a previously established relationship with peak current (See supporting information) is around $1.4 \times 10^{12}$ oligonucleotides/$cm^2$ (for an average anchoring oligonucleotides of ≤5 nm).

Modular signaling oligonucleotides. Experiments using the modular signaling oligonucleotide (FIG. 10C) were performed using the same protocol than when using the original signaling oligonucleotide expect for the addition of 20 mM of $MgCl_2$ in the sample. The nucleic acid sequence of the oligonucleotides used is show in Table 2. A concentration of 100 nM of modular signalling oligonucleotide was used in all experiments. Experiments performed in buffer used 50 mM sodium phosphate, 150 mM NaCl, pH 0.7.0 while experiments in whole blood used bovine whole blood samples.

TABLE 2

Sequences of different DNA oligonucleotides for
modular signaling oligonucleotides experiments
(see FIG. 10)

Anchoring oligonucleotides

| | |
|---|---|
| A1, A3, A4 | 5'-HS-$(CH_2)_6$- TCAG TAG GAG AGT GGA (SEQ ID NO: 7) |
| A2 | 5'-HS-$(CH_2)_6$- CCGG AAA GGG AAG AAG (SEQ ID NO: 8) |

Signaling oligonucleotides

| | |
|---|---|
| A1 | DNP-5'-TCCACTCTCCTACTGA-MB (SEQ ID NO: 9) |
| A2 | NWFDITNWLWYIKKKKGS-5'-CTTCTTCCCTTTCCGG-MB (SEQ ID NO: 10 - SEQ ID NO: 4) |

TABLE 2 -continued

Sequences of different DNA oligonucleotides for
modular signaling oligonucleotides experiments
(see FIG. 10)

| | |
|---|---|
| A3 | labeling element: NWFDITNWLWYIKKKKGS-5'-CCTTAACCCGTTTGCC-3' (SEQ ID NO: 10 - SEQ ID NO: 11) adaptor element: 5'-GGCAAACGGGTTAAGGTCCACTCTCCTACTGA-3'-MB (SEQ ID NO: 12) |
| A4 | labeling element: 5'-CCTTAACCCGTTTGCC-3'-NWFDITNWLWYIKKKKGS (SEQ ID NO: 11 - SEQ ID NO: 10) adaptor element: 5'-GGCAAACGGGTTAAGGTCCACTCTCCTACTGA-3' -MB (SEQ ID NO: 12) |

Electrochemical Measurements. Electrochemical measurements were performed at room temperature using a EmStatMUX potentiostat multiplexer (Palmsens Instruments, Netherland) and a standard three-electrode cell containing a platinum counter electrode (gauze-Sigma-Aldrich) and a Ag/AgCl (3M NaCl) reference electrode (CHI). The bio-electrochemical interfaces were fabricated as described above using a high anchoring oligonucleotide density (1.4× $10^{12}$ oligonucleotides/$cm^2$). The gold surface was then covered using a MCH self-assembled monolayer (SAM). Experimental data were collected using square wave voltammetry from −0.05 to −0.45V in increments of 0.001V vs. Ag/AgCl, with an amplitude of 50 mV and a frequency of 60 Hz. Peak currents were fit using the manual fit mode in the PSTrace software (of Palmsens Instrument). All measurements were taken immediately after adding 100 nM of the signaling oligonucleotides to the sample containing the target proteins (i.e. no pre-incubation was needed between the signaling oligonucleotide and the target). Results are presented in terms of current (knowing that the area of the electrode is 0.03 $cm^2$). Gain represents difference in peak currents obtained before and after target addition divided by initial peak current.

Dose-response curves for individual sensors (FIGS. 2E and 2F) were obtained using 100 nM of signaling DNA by sequentially increasing the target protein concentration. Each 1 ml sample was analyzed simultaneously using three electrodes. Individual dose-response curves were fitted to a single-site binding mechanism ([T]=target concentration; Amp=current amplitude; $C_0$=background current; $C_{50}\%$ is the concentration of proteins at which 50% of the sensor's signaling amplitude was reached:

$$C_{[T]} = C_0 + \left( \frac{[T](Amp)}{[T] + C_{50\%}} \right)$$

Determination of the surface density of the anchoring DNA oligonucleotides (or the average distance between anchoring DNA oligonucleotides). The anchoring-DNA surface density (i.e., the number of electroactive DNA moles per unit area of the electrode surface, $N_{tot}$) was determined using a previously established relationship with peak current as described (O'Connor et al., 1999; Idili et al., 2014):

$$I_{peak}(E_0) = 2nfFN_{tot} \frac{\sinh(nFE_{ac}/RT)}{\cosh(nFE_{ac}/RT) + 1}$$

where $I_{peak}$ ($E_0$) is the average AC peak current in a voltammogram, n is the number of electrons transferred per redox event (with our MB label n=2), F is the Faraday current, R is the universal gas constant, T is the temperature, $E_{ac}$ is the amplitude, and f is the frequency of the applied voltage perturbation. For this procedure, it was assumed that each anchoring oligonucleotide could hybridize to a signaling oligonucleotide and that electron transfer only takes place between methylene blue and the electrode surface upon binding of the signaling DNA oligonucleotide (a perfect electron transfer for each DNA bound methylene blue was assumed). Electrochemical measurements were taken following a 35 minute immersion of the sensors in a solution containing 100 nM of signaling oligonucleotide to achieve the saturation. The peak response corresponding to the methylene blue electron transfer was then used in the above equation to calculate the number of moles of anchoring-DNA. This number was divided by the electrode surface area to obtain the anchoring-DNA surface density in terms of moles/cm$^2$. Considering a circle area around each anchoring-DNA, this area was estimated from reversing the value of density (oligonucleotides/cm$^2$), and consequently the distance was then calculated from the diameter of this circle area.

We controlled the density with which anchoring DNA oligonucleotides are packed on the electrode surface (FIG. 5) by varying the concentration of thiolated oligonucleotide employed during sensor fabrication. When employing fabrication concentrations of 100 nM we reproducibly achieve probe densities around $1.4 \times 10^{12}$ oligonucleotides/cm$^2$.

eSHHA for the one-step detection of proteins. As initial proof-of-principle validation of eSHHA, the assay was adapted for the detection of two large macromolecules: antibodies and streptavidin (FIG. 2). To do so, two 16-base signaling oligonucleotides were designed and labeled at 3' extremity with methylene blue (to generate our electrochemical signaling readout) and at the 5' end with the small hapten digoxigenin (Dig) or biotin that are recognized by anti-Dig antibody (FIG. 2, top-row) and streptavidin (FIG. 2, bottom-row), respectively. The complementary 16-base DNA anchoring oligonucleotide was first immobilized to a gold electrode at high surface coverage via a 5'-C6-thiol group that enables easy attachment via the formation of sulfur-gold bond and then back-filled the surface by using 6-mercaptohexanol. In order to optimize the sensitivity of eSHHA, the minimal concentration of signaling oligonucleotide that is needed to saturate all the anchoring oligonucleotides at the surface of the electrode was determined. The dose-response curve of the these electrodes indicates that the electrode's surface are saturated at a concentration of signaling oligonucleotide of about 100 nM (see FIG. 3), which generates p-amp currents. A 100 nM signaling oligonucleotide concentration was therefore used in all eSHHA experiments since this concentration of signaling oligonucleotide ensures a high, robust electrochemical signal while ensuring detection limits in the low nM (100 nM of target proteins are expected to saturate the sensor since they will sequester 100 nM of signaling oligonucleotides).

The response of eSHHA for the detection of our two model target proteins was then tested. Various samples of proteins were prepared at different concentrations in which 100 nM of signaling oligonucleotide seconds was added before the acquisition. In absence of target protein (FIGS. 2A and 2B, black curve), both sensors produced large Faradaic current over 1 μA in minutes (FIGS. 2C and 2D, black curve–$t_{1/2}$ Antibody=11.6 min and $t_{1/2}$ Streptavidin=11.2 min). In the presence of protein (100 nM) MB-redox current was reduced by 68% and 52%, respectively (FIGS. 2A and 2B, dashed curves). Of note, the hybridization rate of the signaling oligonucleotide was not affected by the presence of the macromolecule (FIGS. 2C and 2D, blue curve–$t_{1/2}$ Antibody=10.5 min; and $t_{1/2}$ Streptavidin=9.7 min, respectively). eSHHA achieved quantitative detection over a 100-fold dynamic range of target concentration slightly below 100 nM (FIGS. 2E and 2F). Dig antibody's sensor (FIG. 2E) displayed a $C_{50\%}$ (concentration of target protein when 50% of the sensor signal is reached) of 27±3 nM, consistent with the fact that half of the signaling oligonucleotide (50 nM) is expected to be bound by 25 nM of antibodies since each antibody contains two binding sites. For the streptavidin sensor (FIG. 2F), a $C_{50\%}$ of 14±2 nM was obtained, which is again consistent with the fact that half of the signaling oligonucleotide (50 nM) should be bound to 12.5 nM of streptavidin since this later contains four binding sites for biotin.

Figure 5A:
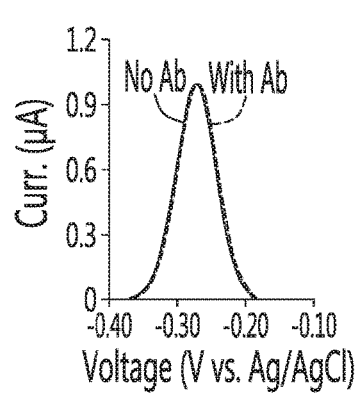
FIG. 5 illustrates that eSHHA's signaling mechanism takes place when the macromolecular entity specifically binds the signaling oligonucleotide. Results are shown as current (μA) in function of voltage (in V, A) or time (in min, B) in the presence (dashed line) and in the absence (regular line) of the macromolecular target (an antibody in this figure). To demonstrate this, a control signaling oligonucleotide that does not possess a moiety for binding a macromolecular entity was designed. This control was tested using the Dig-antibody system. In contrast to the Dig eSHHA sensor (see FIG. 2), the hybridization of this control signaling DNA on the electrode surface was not affected by the presence of the Dig-antibody.
Figure 5B:
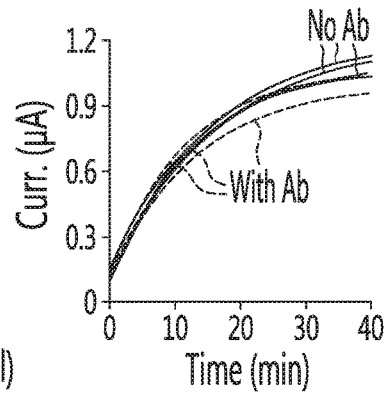
Figure 6:
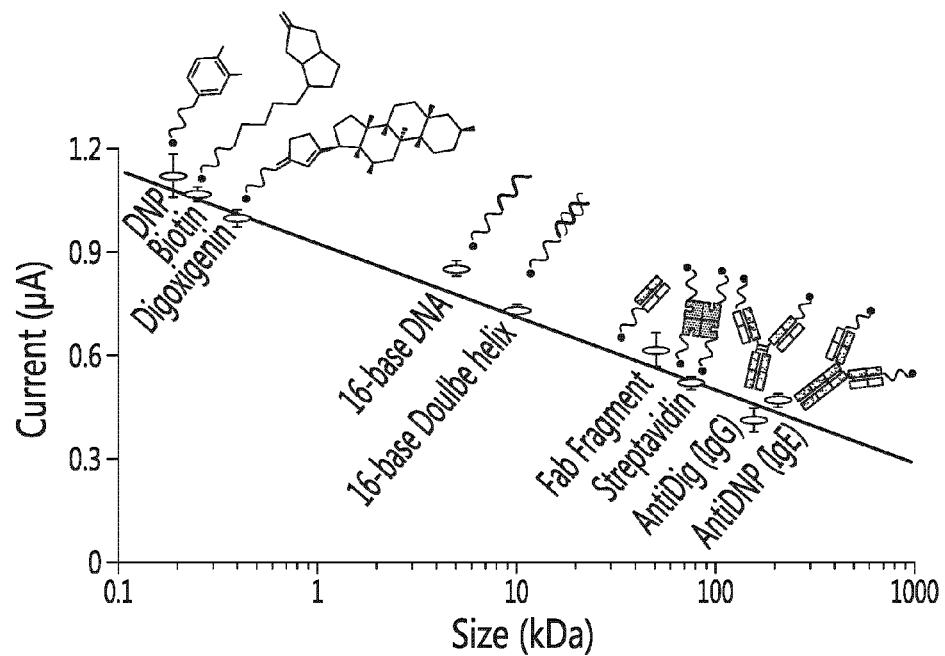
FIG. 6 illustrates that eSHHA's electrochemical signal is inversely correlated with the size of the molecule attached on the signaling oligonucleotide following a semi-logarithmic relationship ($R^2$=0.96). Results are shown as current (μA) in function of size of the moiety for binding a macromolecular entity (kDa). Molecular weights used in this figure include three additional signaling oligonucleotides in the case of the tetravalent streptavidin (three additional biotin binding sites), and one additional signaling oligonucleotide in cases of bivalent antibodies.
Figure 7:
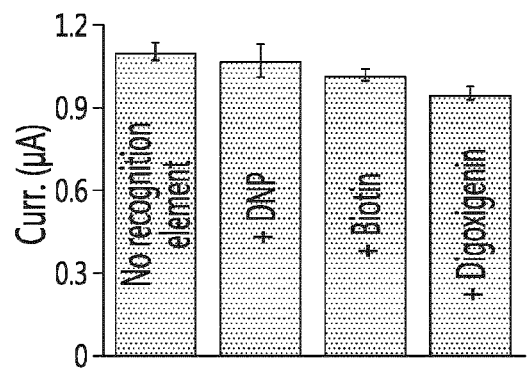
FIG. 7 illustrates steric-hindrance effect created by the attachment of small-sized ligands on the signaling DNA. Results are shown as a measure of current (pA) in function of the moiety for binding a macromolecular entity (referred to as a recognition element on this figure): control ($1^{st}$ column), DNP ($2^{nd}$ column), biotin ($3^{rd}$ column) and digoxigenin ($4^{th}$ column). The attachment of small sized molecules such as 2,4-dinitrophenol (DNP, 184 Da), biotin (244 Da) and digoxigenin (390 Da)) to the signaling oligonucleotide reduces the electrochemical current of eSHHA by 3%, 8% and 13%, respectively.
Figure 8B:
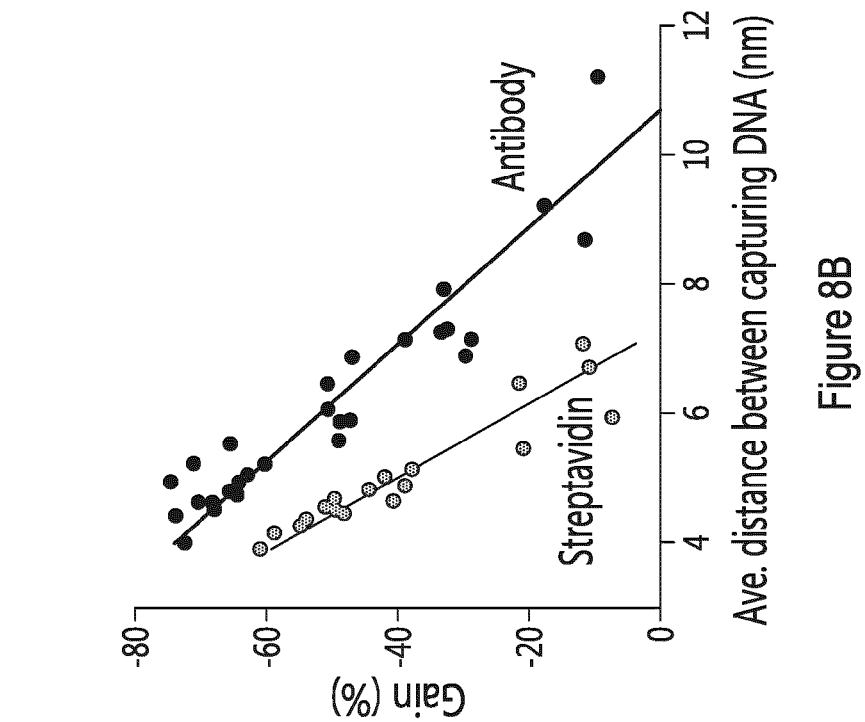
FIG. 8 illustrates that the optimal eSHHA performance is observed at high anchoring oligonucleotide density (low average distance between anchoring oligonucleotide). (A) eSHHA signaling mechanism degrades rapidly when increasing the average distance between the anchoring oligonucleotides with no signaling observed when the average distance between the anchoring oligonucleotides becomes larger than the size of the protein (10-15 nm). Results are shown as current (μA) in function of the presence or absence of the macromolecular target (antibody in this figure). (B) The inverse linear relationship between signal gain and average distance between anchoring oligonucleotides also depends on the target size. For example, larger protein, such as antibodies (≈12 nm), produces more steric hindrance and thus, can function at slightly lower anchoring oligonucleotide density than, for example, the smaller target streptavidin (≈5 nm). These experiments were performed at room temperature in 50 mM $NaH_2PO_4$, 150 mM NaCl, pH 7.0. Results are shown as the gain (% of reduction in current in the presence of the macromolecular entity) in function of the average distance between anchoring oligonucleotide (referred to as capturing DNA, in nM).
Figure 8A:
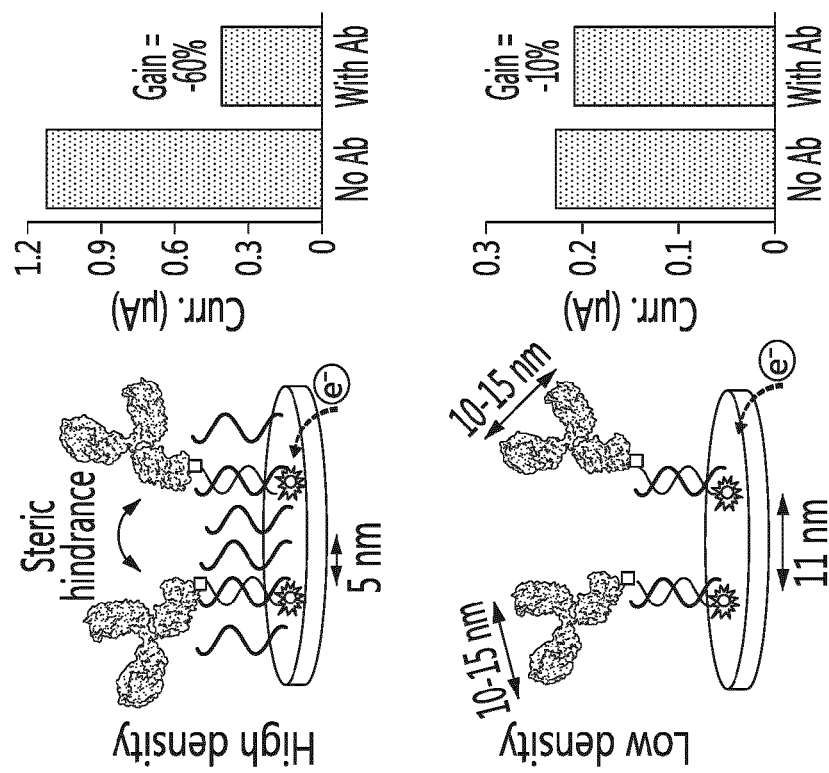
Figure 9C:
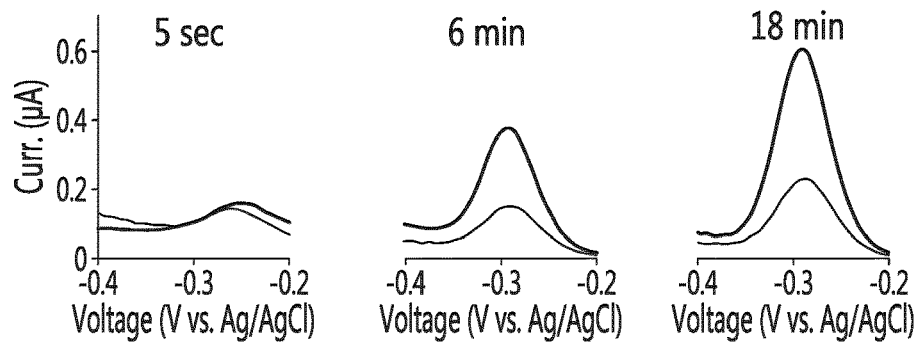

Two key controls were designed to support the proposed novel "steric hindrance" mechanism and to highlight the selectivity of eSHHA. It was first verified that the lower electrochemical signal obtained in presence of the target macromolecule was due to fewer signaling oligonucleotides reaching and hybridizing on the gold surface, rather than to a reduced efficiency in electron transfer resulting from antibody binding to the signaling oligonucleotide. In support of the first hypothesis, no reduction in electrochemical signal was observed following the addition of saturating concentration of macromolecule target on the electrode's surface previously saturated with the signaling oligonucleotide (FIG. 4). It was further confirmed that this signal reduction in presence of the target macromolecule is produced through the specific binding of the macromolecule to the signaling oligonucleotide. To do so, a signaling oligonucleotide that contains no specific recognition element was used and provided an electrochemical signal of similar intensity whether in presence or absence of target macromolecule (FIG. 5). This result confirmed that the signal reduction observed in eSHHA is not linked to the unspecific protein binding on the electrode's surface.

eSHHA is sensitive to the size of the target macromolecules. The electrochemical signaling of eSHHA is proportional to the size of the target macromolecule. Since larger macromolecules produce more steric-hindrance effect between the signaling and the anchoring oligonucleotides near the electrode's surface, these produce a larger signal decrease. This was demonstrated by comparing the electrochemical signal produced by signaling oligonucleotides attached to molecules of increasing molecular weights (i.e. from 184 Da and up to 180,000 Da) (FIG. 6). For example, the attachment of small size molecules like 2,4-dinitrophenol (184 Da), biotin (244 Da) and digoxigenin (390 Da), to the signaling oligonucleotide reduced the electrochemical current by 3%, 8% and 13%, respectively (see also FIG. 7). Attachment of a 16-base DNA sequence (5,000 Da) reduced the current by 30%, while the binding (through recognition element) of large macromolecules, such as Fab fragment (50,000 Da), streptavidin (75,000 Da: this MW includes the weight of three additional biotin-bearing signaling oligonucleotides that bind to the three additional biotin binding sites), and antibodies (such as IgG and IgE ~150 kDa) reduced the current by 40%, 50% and 60%, respectively (See also FIG. S5). It was therefore found that the electrochemical signal generated by the eSHHA (which is linked to the number of signaling oligonucleotides hybridizing on the electrode's surface) is inversely correlated with the size of the target macromolecule, following a semi-logarithmic relationship (FIG. 6). This result illustrates that eSHHA will enable optimal signal gain reduction when the molecular weight difference between the recognition element and the target macromolecule is maximized.

eSHHA works optimally at high density of anchoring oligonucleotides on the electrode's surface. Additional evidence supporting the steric hindrance mechanism of eSHHA also came from the demonstration that eSHHA only performs well with a densely-packed layer of anchoring oligonucleotides. Accordingly, a poorer performance would be expected with a low covered surface since a bound or free signaling oligonucleotide should equally hybridize with a anchoring oligonucleotide regardless of its binding to large-sized molecules. To confirm this, several electrodes were functionalized with varying concentrations of anchoring oligonucleotide in order to modify coverage density (FIG. 8). It was found that the signal gain rapidly (linearly) degrades upon increasing the average distance between the anchoring oligonucleotides (FIG. 8B). For example, the electrode with a densely-packed layer of anchoring oligonucleotides on its surface (average distance of 5 nm between oligonucleotides) provided a high electrochemical current (1.1 µA) as well as a −60% signal gain reduction in presence of the target antibody (FIG. 8A, top). In contrast, electrodes with a low packed layer of anchoring oligonucleotide (average distance of 11 nm between oligonucleotides) provided low electrochemical signals (0.2 µA) and thus, a resulting limited signal gain reduction in presence of antibody (−10%) (FIG. 8A, bottom). These results are in contrast with previously reported e-DNA sensors for which the signal was found to degrade rapidly when the anchoring oligonucleotide was used at high surface coverage. As expected, the inverse linear relationship between signal gain and average distance between anchoring oligonucleotides was also found dependent on the target size (FIG. 8B). Indeed, when lowering the density of anchoring oligonucleotides at the surface of the electrode (i.e. increasing the average distance between anchoring oligonucleotides), eSHHA's performance declined more abruptly with smaller-size targets (i.e. streptavidin) compared to larger-size target (i.e. antibody). This is consistent with the fact that smaller proteins will generate less steric hindrance at the electrode's surface, and thus will become undetectable when the average distance between anchoring oligonucleotides is larger than the protein size.

eSHHA works directly in whole blood. eSHHA works directly in whole blood and enables the simultaneous detection of multiple proteins in less than 10 minutes. One of the most important advantages of eSHHA is that unlike previously reported single-step methods for detection of macromolecules, it is selective enough to be employed directly in whole blood (FIG. 9). It was first showed that eSHHA's performance is nearly identical in terms of gain and kinetic when deployed directly in whole blood or simply in a buffered solution (100 nM of antibody) (FIG. 9A). Another considerable advantage of our eSHHA compared to previously published electrochemical DNA-based assays for the detection of antibodies is that no rapid drift (or change in current) is detected when the sensor is first inserted in whole blood. This is due to the fact that the methylene blue redox label is not present on the electrode's surface but rather on the signaling oligonucleotide. Therefore, no electrochemical signal will be generated before the signaling oligonucleotides migrate and hybridize to the surface-bound anchoring oligonucleotide.

eSHHA can also be adapted for the simultaneous detection of multiple proteins in complex matrices, such as whole blood. This was demonstrated by simultaneously employing, in the same blood sample, several electrodes containing different anchoring oligonucleotide sequences. These different electrodes were each associated to a complementary specific signaling oligonucleotide linked to a specific recognition element. We demonstrated this multi-detection feature by carrying out measurements of two antibodies (anti-Dig and anti-DNP) in whole blood samples (FIG. 9B). In anti-Dig spiked-blood sample (FIG. 9B-1), only the electrochemical current of the corresponding blue electrode diminished (−60% gain reduction) while the signal of the two other electrodes (anti-DNP and Ctrl) remained unchanged (the control signaling oligonucleotide contains no recognition element). Similarly, in anti-DNP spiked-blood (FIG. 9B-2), only the electrochemical current of the corresponding green electrode diminished (−50% gain reduction). A third blood sample, spiked with both anti-Dig and anti-DNP antibodies, generated a eSHHA response in which both the blue and green electrodes give a significant electrochemical signal gain, while the control "black" electrode remained unchanged. Although the electrochemical signal reached equilibrium after a 50-min incubation, optimal gain reduction is already attained within the first 10 minutes (FIG. 9B; center). A kinetic of current density in function of voltage indicates that, in whole blood, as little as 6 minutes may be required to obtain a differential signal (FIG. 9C). Taken together, these results clearly demonstrate the high potential of the eSHHA mechanism as a one-step, easy-to-use assay for the rapid detection of multiple proteins in complex matrices.

Figure 10B:
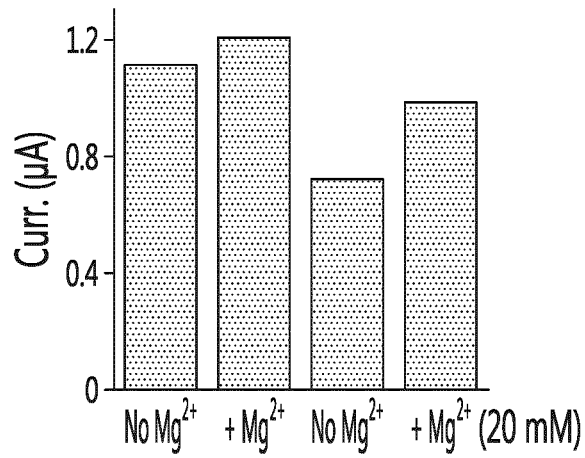
Figure 10C:
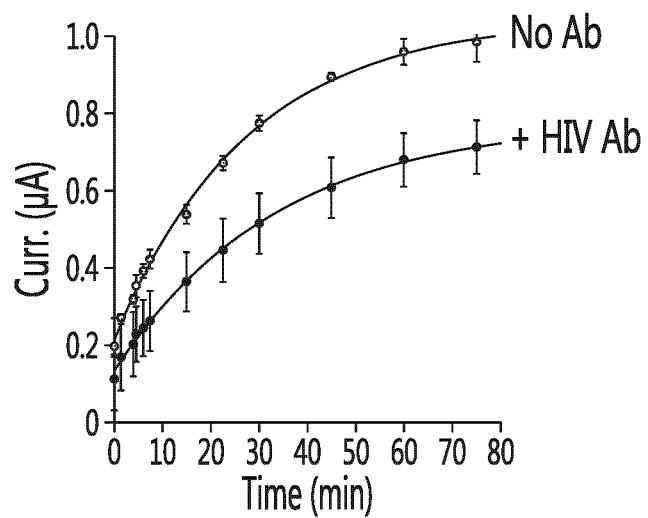

The sensor using a peptide as a recognition element employed a modular signaling oligonucleotide (e.g., which contains an adaptor element and a labeling element) (FIG. 10). Due to their larger size and higher charge density, less of modular signaling oligonucleotide (33%) can hybridize on the electrode surface (due to steric hindrance and charge repulsion) (FIG. 10B). However, the addition of 20 mM of Mg2+ (MgCl) in the sample enables to reduce charge repulsion and help increase the hybridization efficiency of such modular signaling oligonucleotide by up to 25%. (C) Detection of anti-HIV antibody (4E10, 1000 nM) using a peptide from the HIV GP41 protein as a recognition element (NWFDITNWLWYIKKKKGS (SEQ ID NO: 10, Brunel et al., 2006). These experiments were performed using 100 nM of modular signaling oligonucleotide, 20 mM MgCl directly in spiked bovine whole blood.

A new a new generalizable, highly selective signal transduction mechanism for the one-step detection of proteins based on steric hindrance effect at the nanoscale was herein described. This signaling mechanism, which exploits the high specificity and selectivity of DNA hybridization, can be adapted, in principle, for the detection of any proteins having a small recognition element that can be attached to DNA. Here we show that eSHHA enables the one-step detection of five different macromolecules (>50 kDA) directly in whole blood with larger proteins generating signal gain reduction down to −65% (FIG. 6). It is believed that eSHHA could also be adapted to support the use of peptides and other small ligands as the recognition elements. eSHHA responds rapidly (<10 min) and sensitively to their targets at low nanomolar concentrations. It also enables multiplexed detection of numerous target proteins simultaneously in a unique sample due to the unique ability that DNA displays to enable the creation of numerous specific anchoring-signaling pair.

eSHHA displays significant advantages over comparable existing protein detection technologies. For example, eSHHA generates electrochemical signal that are 10 times larger than the recently developed E-Ab sensors and electrochemical switches. Since the electrochemical signals is promoted by the specific hybridization of the signaling oligonucleotide to the electrode, it is shown herewith that no signal drift when employed directly in whole blood. eSHHA also displays many advantageous feature when compared to other current methods for the quantitative detection of antibodies such as ELISAs, Western Blots and fluorescence polarization assays. It does not require multi-step, wash- and reagent-intensive processes, does not need specialized technicians and it requires only several minutes to perform and a very inexpensive portable potensiostat. eSHHA also appears more convenient than immunochemical dipsticks given its quantitative feature and its ability to support multiplexed detection in a single sample. Given all these advantages, eSHHA appears to be well positioned for adaptation to point-of-care diagnostics.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Brunel, F. M.; Zwick, M. B.; Cardoso, R. M. F.; Nelson, J. D.; Wilson, I. A.; Burton, D. R.; Dawson, P. E. J. Virol. 2006, 80, 1680-1687

Cash, K. J.; Ricci, F.; Plaxco, K. W. Chem. Comm. 2009a, 41, 6222-4.

Cash, K. J.; Ricci, F.; Plaxco, K. W. J Am Chem Soc 2009b, 131, 6955-7.

Fan C, Plaxco K W, Heeger A J. Electrochemical interrogation of conformational changes as a reagentless method for the sequence-specific detection of DNA. Proc Natl Acad Sci USA. 2003 Aug. 5; 100(16):9134-7. Epub 2003 Jul. 16.

Lass-Napiorkowska A, Heyduk E, Tian L, Heyduk T. Detection methodology based on target molecule-induced sequence-specific binding to a single-oligonucleotideed oligonucleotide. Anal Chem. 2012 Apr. 3; 84(7):3382-9. doi: 10.1021/ac3001034. Epub 2012 Mar. 22.

O'Connor, S. D.; Olsen, G. T.; Creager, S. E. Journal of Electroanalytical Chemistry 1999, 466, 197.

Idili, A.; Amodio, A.; Vidonis, M.; Feinberg-Somerson, J.; Castronovo, M.; Ricci, F. Analytical chemistry 2014, 86, 9013.

Vallée-Bélisle, A.; Ricci, F.; Uzawa, T.; Xia, F.; Plaxco, K. W. J Am Chem Soc 2012, 134, 15197-200.

White, R. J.; Phares, N.; Lubin, A. A.; Xiao, Y.; Plaxco, K. W. Langmuir 2008, 24, 10513-8.

Xiao, Y.; Lai, R. Y.; Plaxco, K. W. Preparation of Electrode-Immobilized, Redox-Modified Oligonucleotides for Electrochemical DNA and Aptamer-Based Sensing. Nat Protoc 2007, 2, 2875-2880.

International application WO 2012/071344 by Vallée-Bélisle et al.

International application WO 2007/120299 by Xiao et al.

---

What is claimed is:

1. A system for detecting a target in sample, said system comprising:
   a plurality of anchoring oligonucleotides each having a nucleic acid sequence, a first end and a second free end;
   a first substrate having a surface associated with, at a plurality of discrete locations, each of the first end of the plurality of anchoring oligonucleotides; and
   a plurality of signaling oligonucleotides,
   wherein each of the signaling oligonucleotide has three distinct segments:
      a core nucleic acid sequence which is substantially complementary to a region of each of the anchoring oligonucleotides and is capable of hybridizing with the anchoring oligonucleotide;
      a first end being associated with a moiety for binding a macromolecular entity; and
      a second end being associated with a reporter moiety; and
   is configured such that, upon hybridizing with the anchoring oligonucleotide, the second end of the signaling oligonucleotide is proximate to the first end of the anchoring oligonucleotide;
   wherein the density of the plurality of anchoring oligonucleotides on the first substrate prevents or limits the formation of a complex between at least one anchoring oligonucleotide, at least one signaling oligonucleotide and the macromolecular entity at two adjacent locations on the first substrate.

2. The system of claim 1, wherein the target is the macromolecular entity.

3. The system of claim 2, wherein the macromolecular entity is a polypeptide.

4. The system of claim 3, wherein the polypeptide is an antibody.

5. The system of claim 4, wherein the moiety for binding the macromolecular entity comprises an epitope specifically recognized by the antibody.

6. The system of claim 1, further comprising a macromolecular entity capable of specifically binding the target.

7. The system of claim 6, wherein the moiety for binding the macromolecular entity is the target.

8. The system of claim 7, wherein the macromolecular entity is an antibody specifically recognizing the target.

9. The system of claim 8, wherein the moiety for binding the macromolecular entity comprises an epitope specifically recognized by the antibody.

10. The system of claim 6, wherein the macromolecular entity is an aptamer specifically recognizing the target.

11. The system of claim 10, wherein the moiety for binding the macromolecular entity comprises a nucleic acid molecule for hybridizing with the aptamer.

12. The system of claim 1, wherein the first end of each of the anchoring oligonucleotides is covalently associated to the surface of the first substrate.

13. The system of claim 12, wherein the first end of the anchoring oligonucleotide is a nucleic acid terminus.

14. The system of claim 1, wherein the first substrate is a metallic electrode.

15. The system of claim 1, wherein the core nucleic acid sequence of the signaling oligonucleotide is complementary to the nucleic acid sequence of the anchoring oligonucleotide over the entire length of the anchoring oligonucleotide.

16. The system of claim 1, wherein each of the signaling oligonucleotide comprises at least 10 nucleic acid bases.

17. The system of claim 1, wherein the reporter moiety is a redox-reporter.

18. The system of claim 1 for detecting a plurality of distinct targets, said system further comprising:
   a plurality of types of anchoring oligonucleotides each anchoring oligonucleotide type having a distinct nucleic acid sequence, a first end and a second free end;
   a plurality of substrates, each of the substrate having a surface associated with, at a plurality of discrete locations, with the first end of a single type of anchoring oligonucleotides and each of the substrates having a different type of anchoring oligonucleotide; and a plurality of types of signaling oligonucleotides, wherein each type of the signaling oligonucleotides has three distinct segments:
- a core nucleic acid sequence substantially complementary to a region of a corresponding anchoring oligonucleotides and is capable of hybridizing with the corresponding anchoring oligonucleotide;
- a first end being associated with a distinct moiety for binding a distinct macromolecular entity; and
- a second end being associated with a reporter moiety; and is configured such that, upon hybridizing with the corresponding anchoring oligonucleotide, the second end of the signaling oligonucleotide is located in the vicinity of the first end of the anchoring oligonucleotide;

wherein the density of the anchoring oligonucleotides on each of the plurality substrates prevents or limits the formation of a complex between at least one anchoring oligonucleotide, at least one signaling oligonucleotide and the macromolecular entity at two adjacent locations on each of the plurality of substrates.

19. The system of claim 1, further comprising:
- a second substrate having a surface associated, at a plurality of discrete locations, with each of the first end of the plurality of anchoring oligonucleotides; and
- a plurality of negative control oligonucleotides, wherein each of the plurality of the negative control oligonucleotides has three distinct segments:
  - a core nucleic acid sequence substantially complementary to a region of the anchoring oligonucleotide and is capable of hybridizing with the anchoring oligonucleotide;
  - a first end lacking the moiety for binding a macromolecular entity; and
  - a second end having the reporter moiety; and is configured such that, upon hybridizing with the anchoring oligonucleotide the second end of the signaling oligonucleotide is located in the vicinity of the first end of the anchoring oligonucleotide;

the density of the plurality of the anchoring oligonucleotides on the second substrate is similar to the density of the plurality of the anchoring oligonucleotides on the first substrate.

20. A method for the detection of a target in a sample, said method comprising:
- providing the sample suspected of having the target;
- providing the system of claim 1;
- providing or determining a control amount of the plurality of anchoring oligonucleotides having hybridized with the plurality signaling oligonucleotides in the system in the absence of the target;
- contacting the sample with the system;
- determining a test amount of the plurality of anchoring oligonucleotides having hybridized with the plurality signaling oligonucleotides in the system in the presence of the sample;
- characterizing the sample as having the target if it is determined that the test amount is lower than the control amount and as lacking the target if it is determined that the test amount is equal to or higher than the control amount.

* * * * *